United States Patent
Liu et al.

(10) Patent No.: US 11,100,683 B2
(45) Date of Patent: Aug. 24, 2021

(54) IMAGE COLOR ADJUSTMENT METHOD AND SYSTEM

(71) Applicant: SHANGHAI UNITED IMAGING HEALTHCARE CO., LTD., Shanghai (CN)

(72) Inventors: Wenqing Liu, Shanghai (CN); Qi Duan, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 64 days.

(21) Appl. No.: 16/251,052

(22) Filed: Jan. 17, 2019

(65) Prior Publication Data
US 2019/0156526 A1    May 23, 2019

Related U.S. Application Data

(63) Continuation of application No. PCT/CN2017/089690, filed on Jun. 23, 2017.

(30) Foreign Application Priority Data

Dec. 28, 2016 (CN) .......................... 201611240265.4

(51) Int. Cl.
*G06T 11/00* (2006.01)
*G06T 7/00* (2017.01)
(Continued)

(52) U.S. Cl.
CPC .......... *G06T 11/008* (2013.01); *G06T 7/0012* (2013.01); *G06T 7/40* (2013.01);
(Continued)

(58) Field of Classification Search
None
See application file for complete search history.

(56) References Cited

U.S. PATENT DOCUMENTS 8,830,263 B2 * 9/2014 Kohara .................. G06T 15/08
345/629
10,004,471 B2 * 6/2018 Madabhushi ...... G01R 33/5601
(Continued)

FOREIGN PATENT DOCUMENTS

CN        101325663 A    12/2008
CN        102881011 A    1/2013
(Continued)

OTHER PUBLICATIONS

Shotton, Jamie, Matthew Johnson, and Roberto Cipolla. "Semantic texton forests for image categorization and segmentation." 2008 IEEE conference on computer vision and pattern recognition. IEEE, 2008. (Year: 2008).*

(Continued)

*Primary Examiner* — Michelle M Entezari
(74) *Attorney, Agent, or Firm* — Metis IP LLC

(57) ABSTRACT

The present application discloses an image processing method and a system thereof. The method and the system may transform a list of color table adjustment parameters into one or more preset texture models, and associate a particular texture model with a particular image through an interactive mode. The method may include: obtaining an image including at least one pixel or voxel, obtaining a texture model, associating the image with the texture model; determining an output color of the at least one pixel or voxel based on the texture model associated with the image; and generating an output image based on the output color. The image processing method and system thereof provided by the present application may effectively improve the adjustment efficiency of the image display effect and the interaction experience.

19 Claims, 15 Drawing Sheets

(51) Int. Cl.
    *G06T 7/40* (2017.01)
    *G06T 7/90* (2017.01)
    *G16H 30/40* (2018.01)
    *G16H 40/60* (2018.01)
    *G06T 19/20* (2011.01)

(52) U.S. Cl.
    CPC ............... *G06T 7/90* (2017.01); *G06T 19/20* (2013.01); *G16H 30/40* (2018.01); *G06T 2200/24* (2013.01); *G06T 2207/10072* (2013.01); *G06T 2210/41* (2013.01); *G06T 2219/2012* (2013.01); *G16H 40/60* (2018.01)

(56) References Cited

U.S. PATENT DOCUMENTS

| | | | |
|---|---|---|---|
| 10,198,872 B2* | 2/2019 | Lurie | G06T 19/20 |
| 10,215,830 B2* | 2/2019 | Kwak | G01R 33/465 |
| 10,842,379 B2* | 11/2020 | Mansi | B33Y 10/00 |
| 2003/0076334 A1* | 4/2003 | Dumitras | H04N 19/23 |
| | | | 345/582 |
| 2003/0095692 A1* | 5/2003 | Mundy | A61B 6/00 |
| | | | 382/128 |
| 2003/0231204 A1 | 12/2003 | Hanggie et al. | |
| 2005/0237336 A1* | 10/2005 | Guhring | G06T 15/04 |
| | | | 345/582 |
| 2007/0229529 A1* | 10/2007 | Sekine | G06T 15/04 |
| | | | 345/582 |
| 2009/0232369 A1* | 9/2009 | Senegas | G06T 15/04 |
| | | | 382/128 |
| 2009/0311655 A1* | 12/2009 | Karkanias | A61B 1/3132 |
| | | | 434/262 |
| 2010/0123714 A1* | 5/2010 | Langeland | G06T 19/00 |
| | | | 345/419 |
| 2014/0078144 A1 | 3/2014 | Berriman et al. | |
| 2016/0196665 A1* | 7/2016 | Abreu | G06T 7/251 |
| | | | 345/427 |
| 2016/0295287 A1* | 10/2016 | Jiang | H04N 21/44008 |
| 2017/0186392 A1 | 6/2017 | Kuo et al. | |
| 2017/0358119 A1* | 12/2017 | Forutanpour | G06T 15/04 |
| 2018/0068178 A1* | 3/2018 | Theobalt | G06T 7/70 |
| 2018/0365876 A1* | 12/2018 | Wimmer | G06T 7/33 |
| 2019/0012796 A1* | 1/2019 | Yamasaki | G06T 7/11 |

FOREIGN PATENT DOCUMENTS

| | | |
|---|---|---|
| CN | 104301621 A | 1/2015 |
| CN | 104796683 A | 7/2015 |
| CN | 105719333 A | 3/2016 |
| CN | 105488819 A | 4/2016 |
| CN | 106204498 A | 12/2016 |
| CN | 106682424 A | 5/2017 |
| WO | 2013179180 A1 | 12/2013 |

OTHER PUBLICATIONS

Gopi Karnam et al., Graphical User Interface Based Computer Aided Diagnosis Tool of Human Brain Tumor Segmentation Through MRI and Validation, International Journal of Applied Engineering Research, 11(5): 3247-3254, 2016.

Kelbyone, Replace Color | Planet Photoshop, Effects, Tutorial in Planet Photoshop, 1-11, 2006.

Extended European Search Report in European Application No. 17886979.8 dated Sep. 26, 2019, 10 pages.

International Search Report in PCT/CN2017/089690 dated Oct. 12, 2017, 2 pages.

First Office Action in Chinese Application No. 201611240265.4 dated Sep. 3, 2018, 16 pages.

* cited by examiner

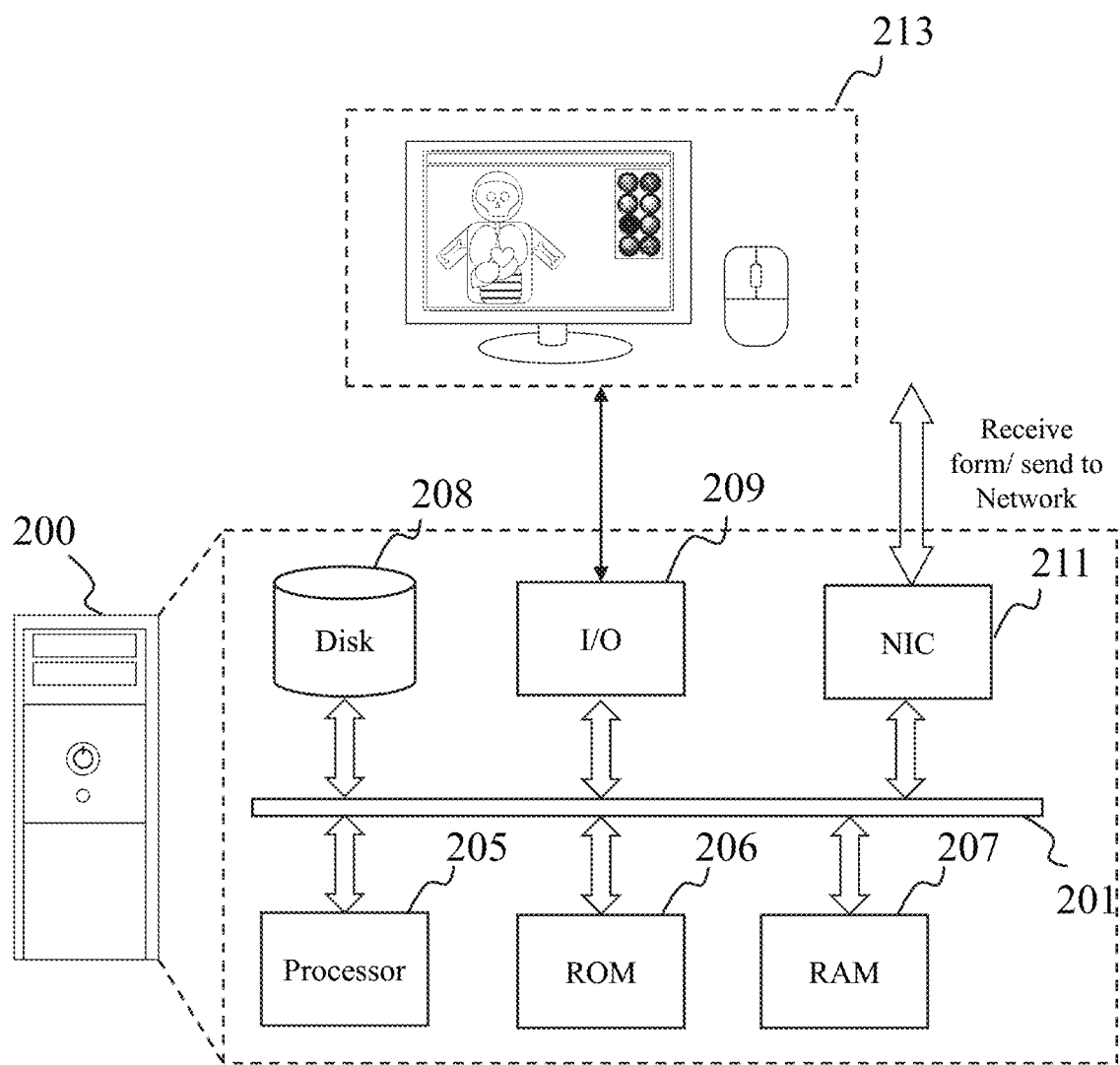
FIG. 2-A

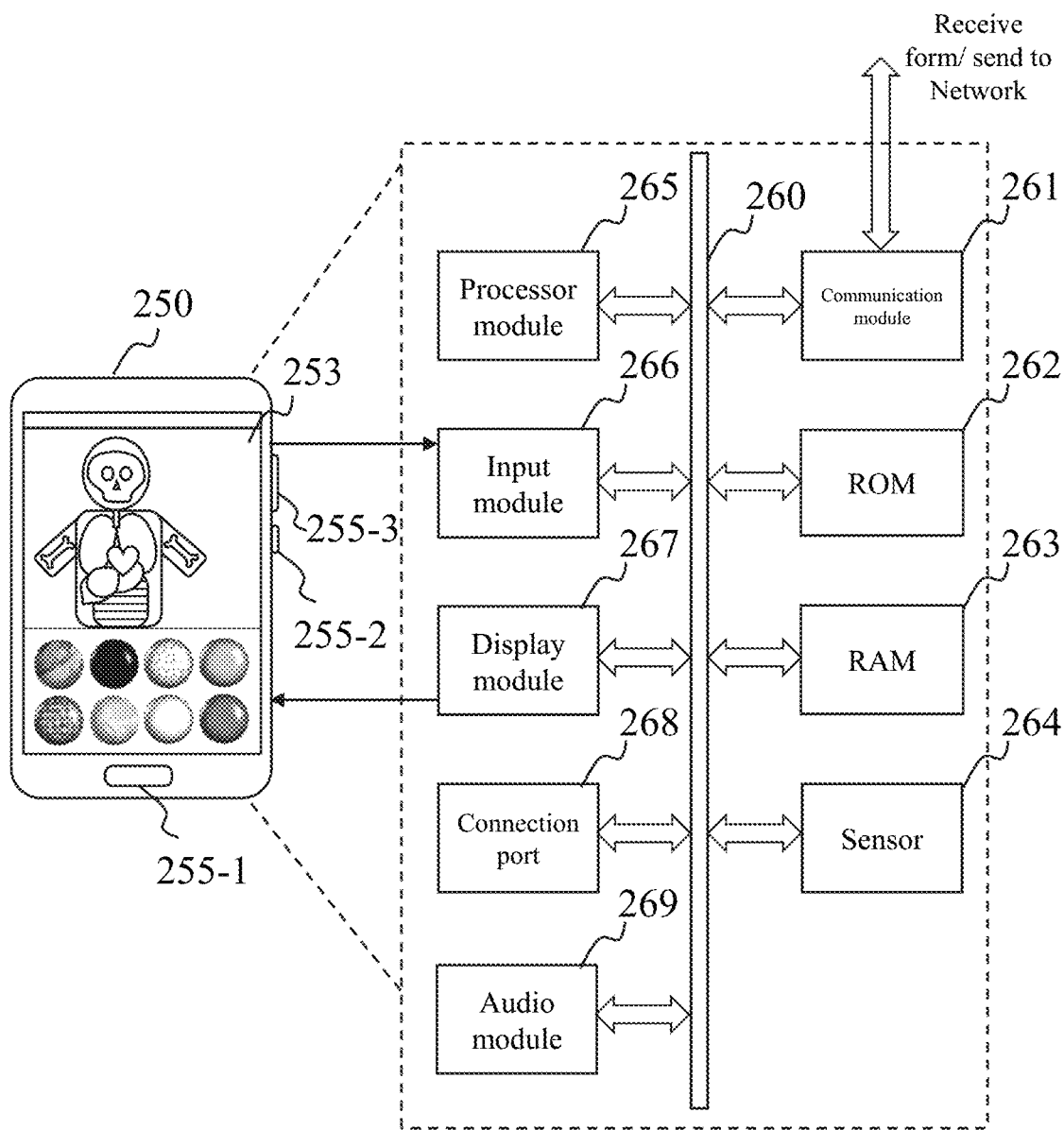
FIG. 2-B

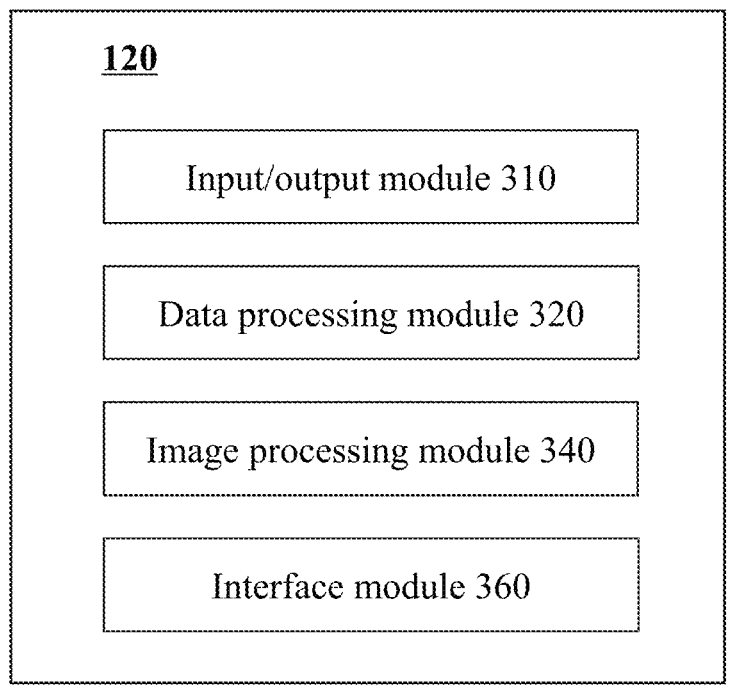
FIG. 3-A
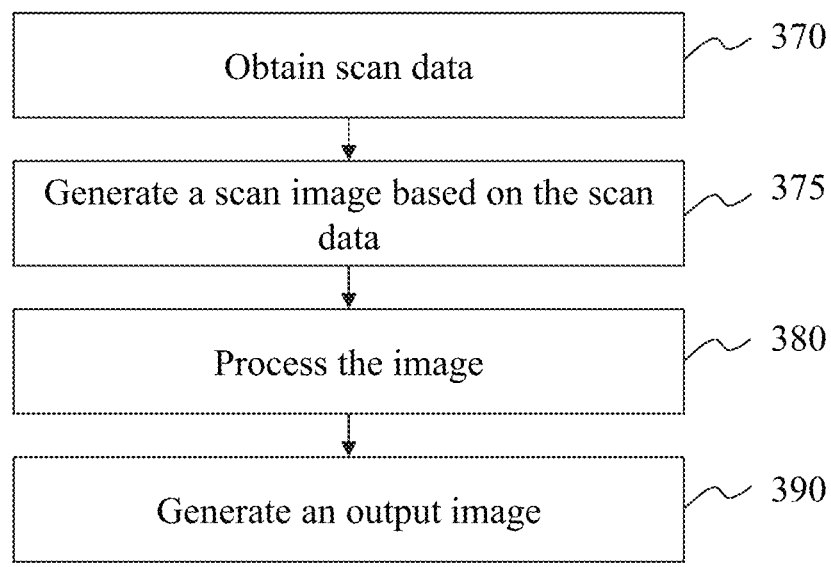
FIG. 3-B

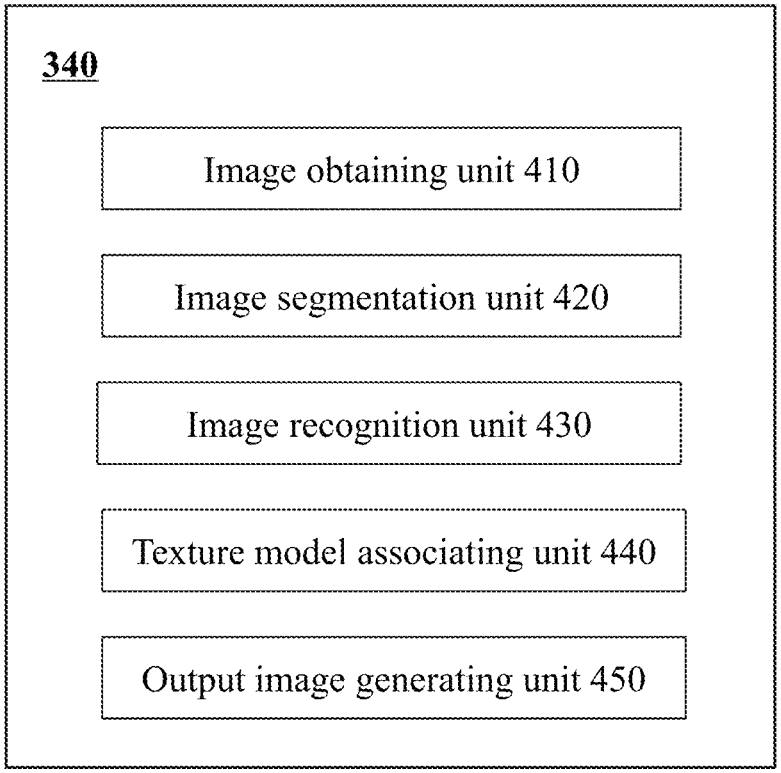
FIG. 4-A
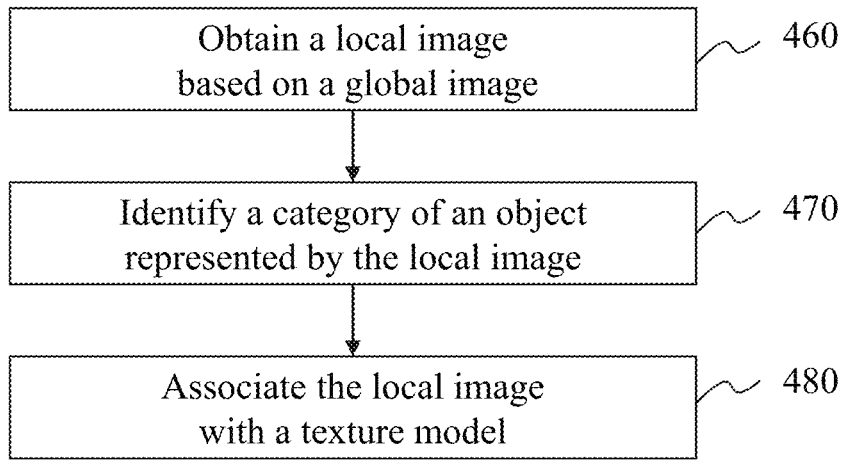
FIG. 4-B

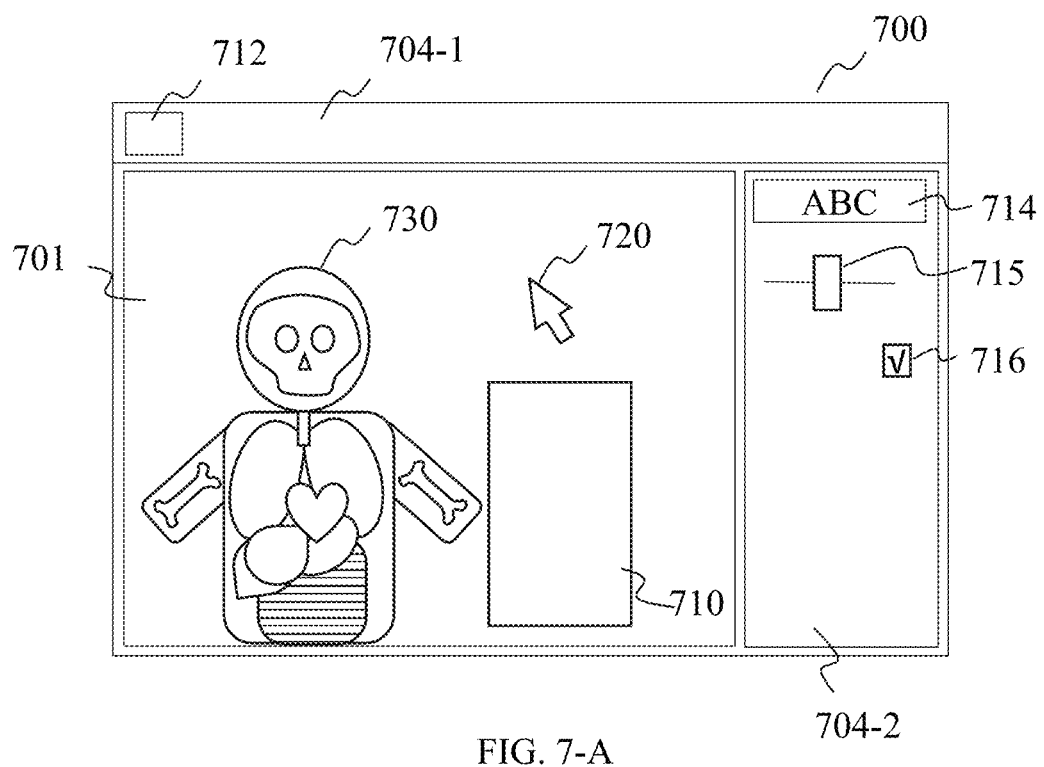
FIG. 7-A
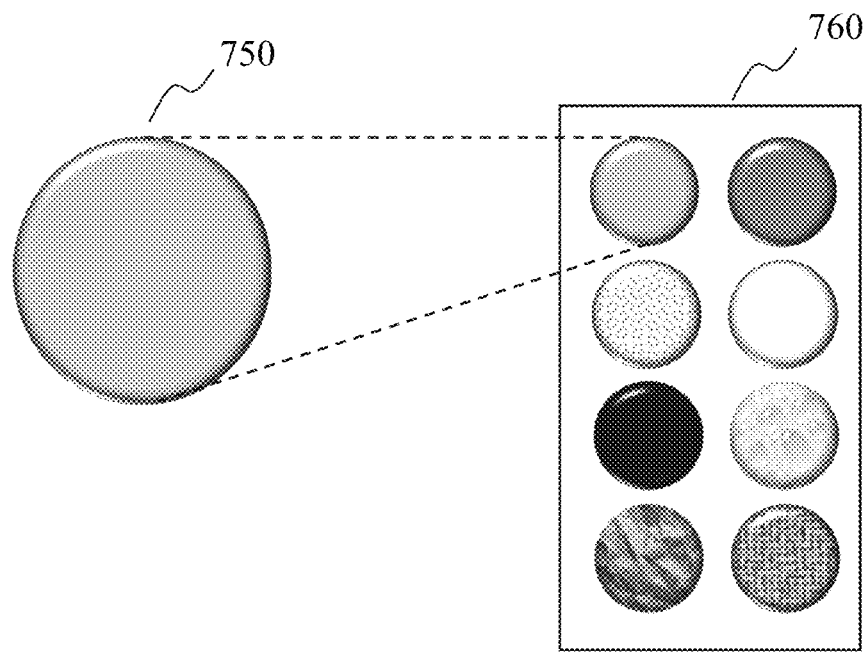
FIG. 7-B

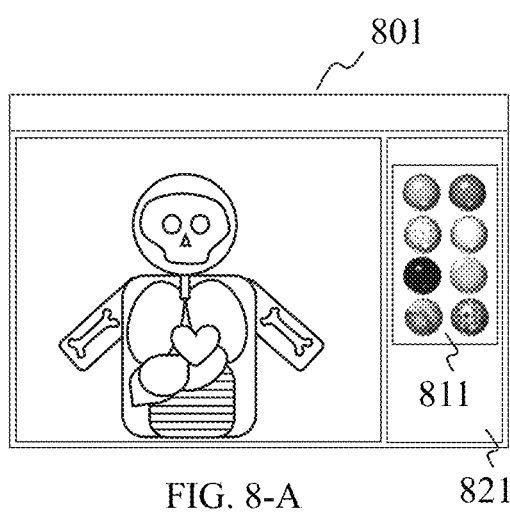
FIG. 8-A
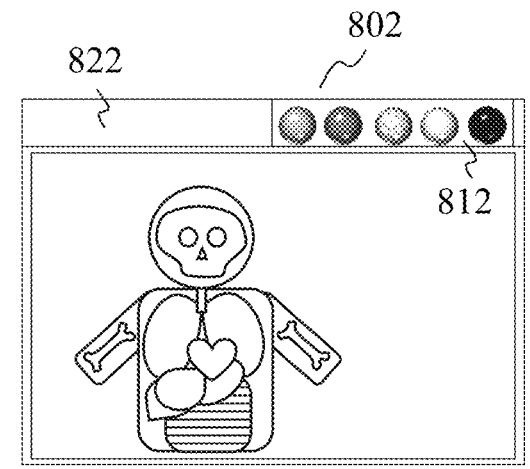
FIG. 8-B
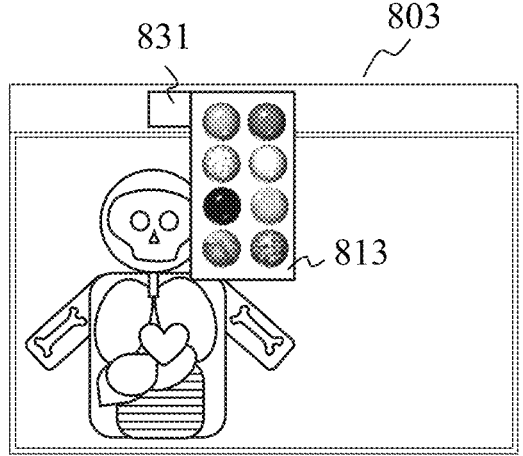
FIG. 8-C
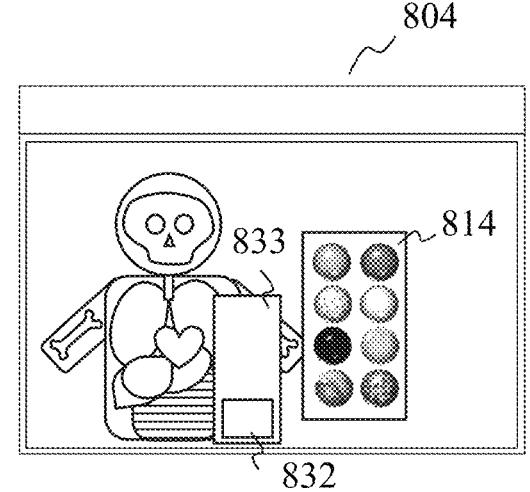
FIG. 8-D
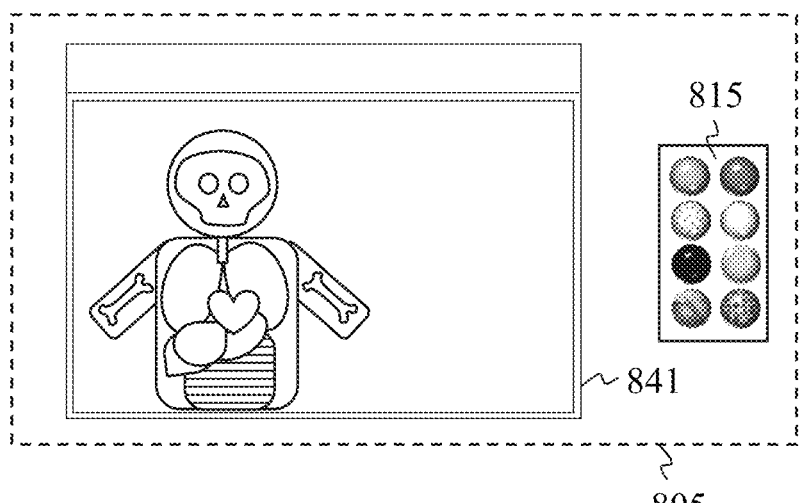
FIG. 8-E

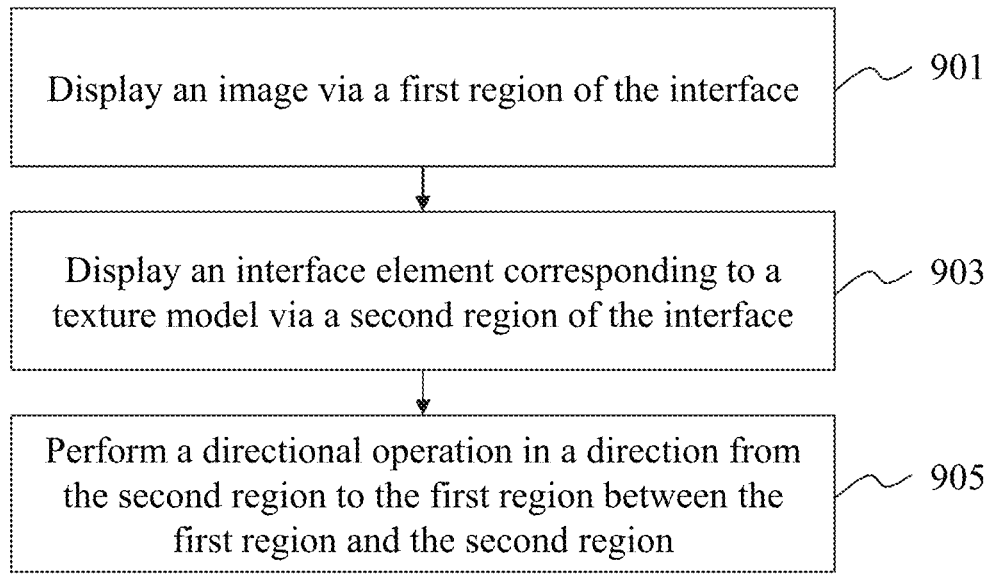
FIG. 9-A
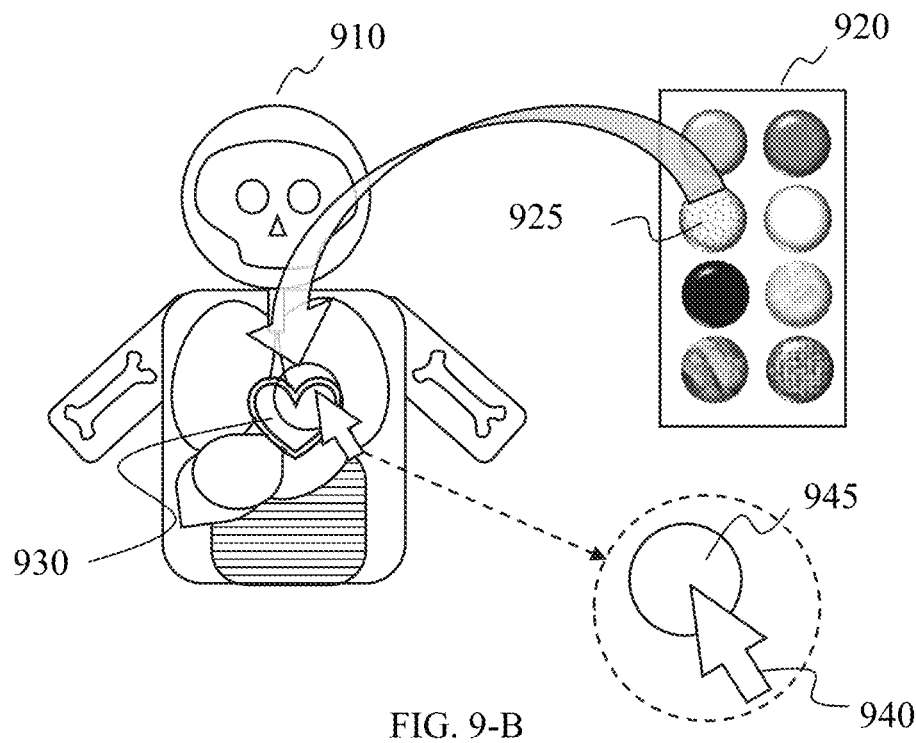
FIG. 9-B

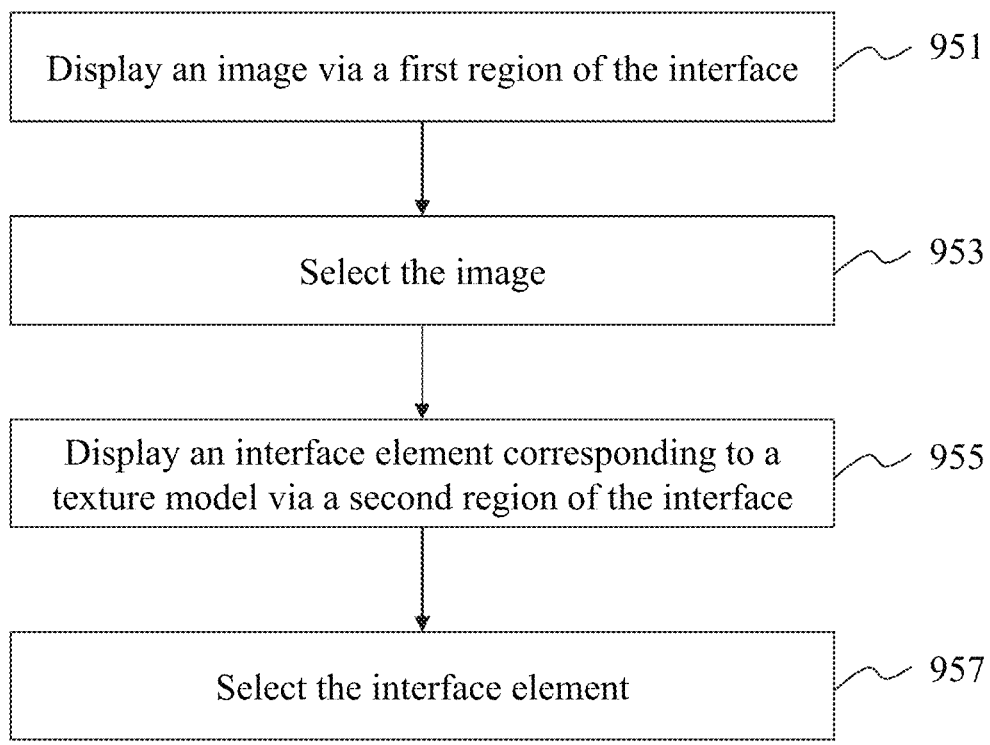
FIG. 9-C
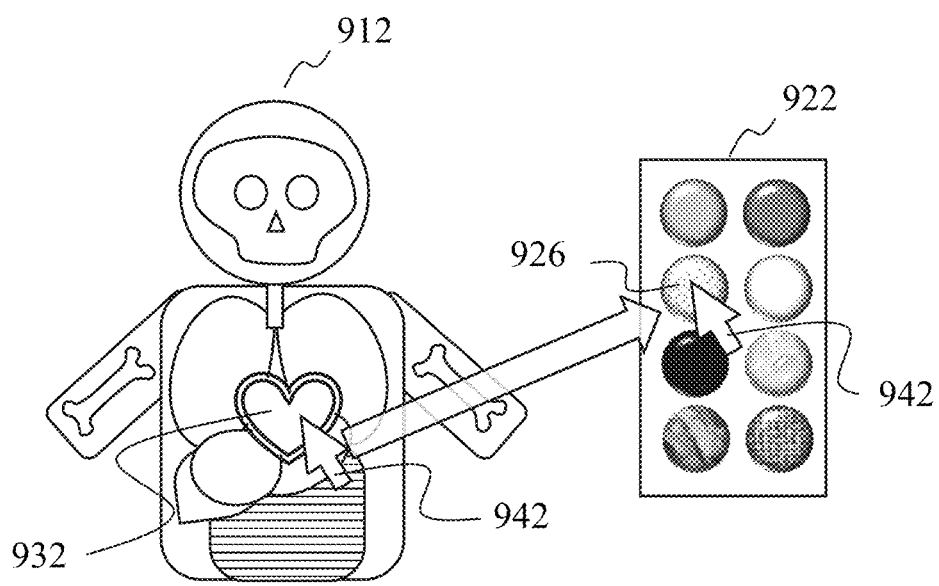
FIG. 9-D

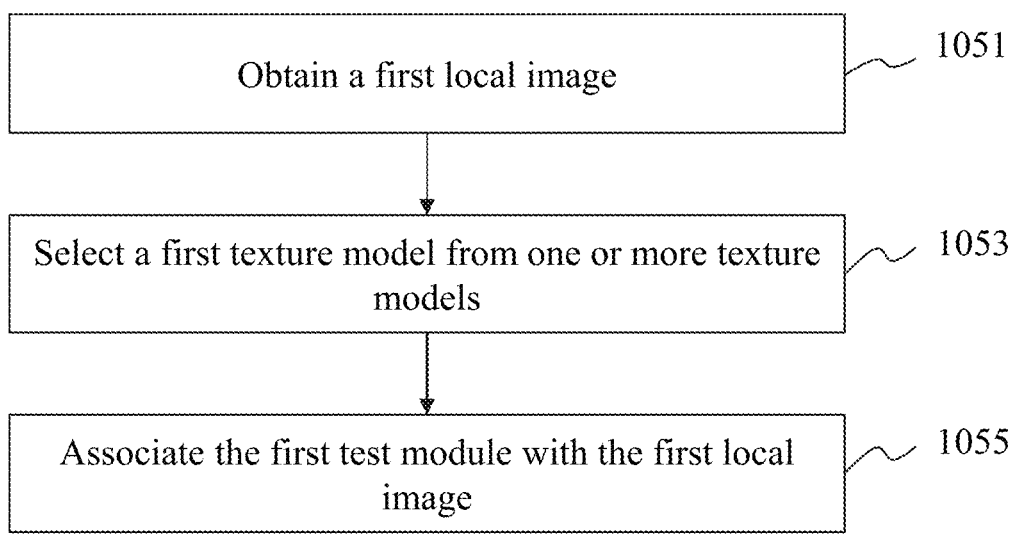
FIG. 10-A

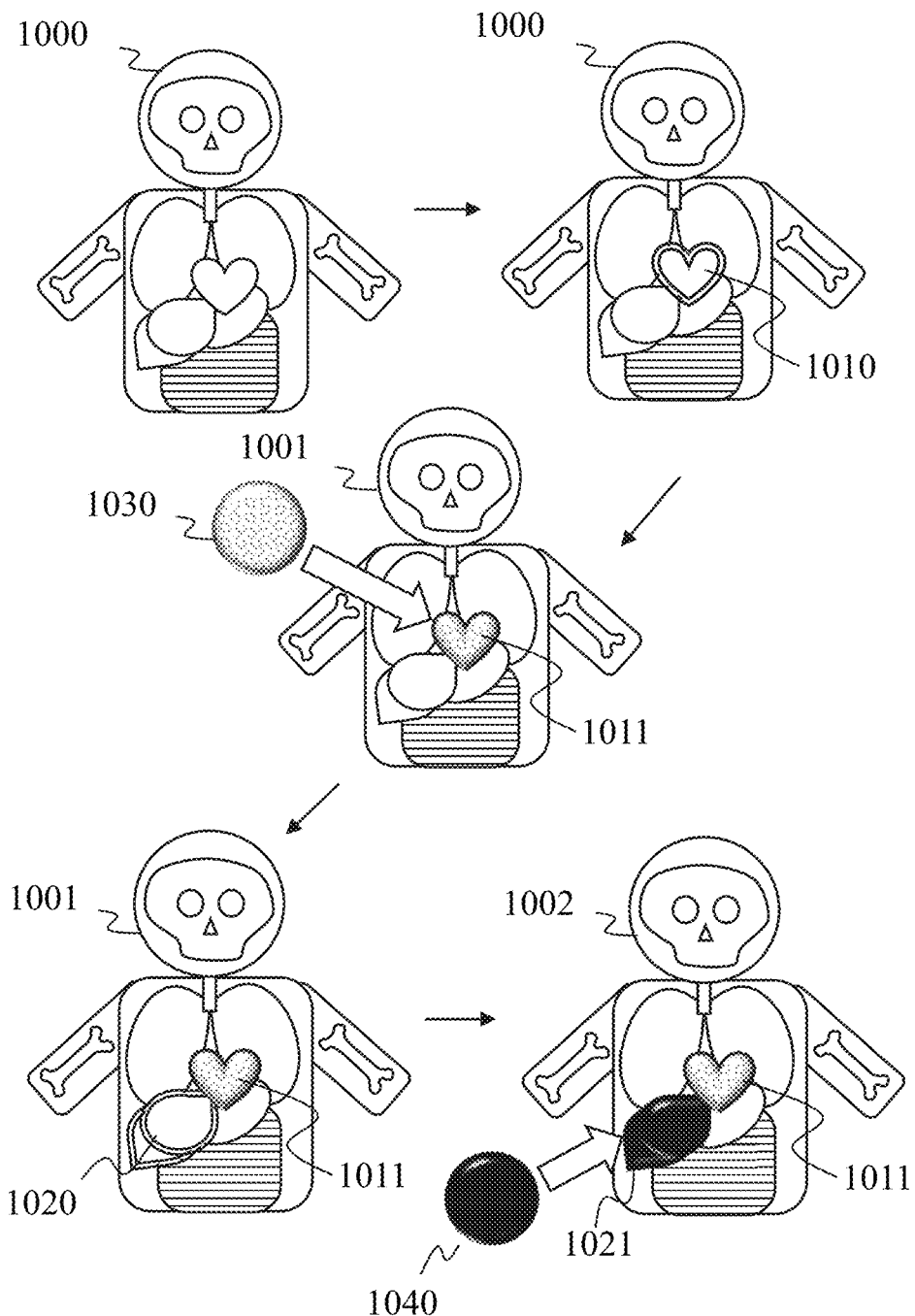
FIG. 10-B

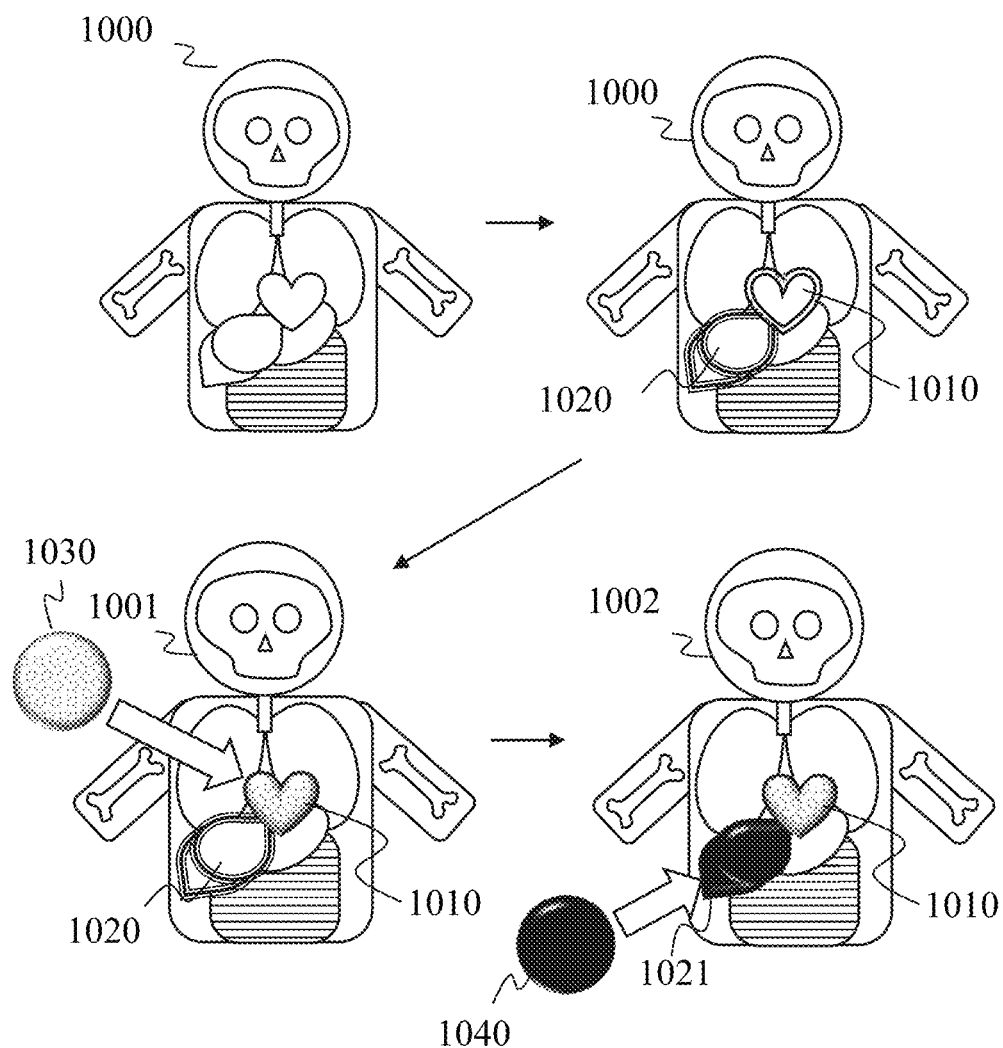
FIG. 10-C

IMAGE COLOR ADJUSTMENT METHOD AND SYSTEM

CROSS-REFERENCE TO RELATED APPLICATIONS

This application is a continuation of International application No. PCT/CN2017/089690 filed on Jun. 23, 2017, which claims priority of Chinese Application No. 201611240265.4 filed on Dec. 28, 2016, the entire contents of which are hereby incorporated by reference.

TECHNICAL FIELD

The present application generally relates to an image processing method and system, and more specifically, to an image color adjustment method and system.

BACKGROUND

During a display of medical three-dimensional slices, editing and interaction of color related parameters are the most frequently used operations. Usually, a user needs to perform a fine adjustment on the color related parameters to obtain a satisfactory display effect. A variety of parameters are involved while adjusting the display effect, for example, hue, brightness, contrast, the number of control points, colors of control points, transparency, lighting conditions (including parameters related to, such as, ambient light, diffuse light, specular light, specular scattering coefficient, shiness), or the like. Various color related parameters are listed in an interface for editing a color effect in a common medical image processing software on the market, so that a user may adjust each specific parameter. However, a non-professional user usually has to adjust the parameters one by one and observe adjusted effects at the same time while adjusting the series of parameters, which reduces efficiency of adjusting the display effect and interactive experience for the user.

In view of the existing problems, there is a need to provide a convenient and quick method for presenting and adjusting an image display effect.

SUMMARY

The present application discloses a method for adjusting a color of an image through a texture model and a system for performing the same. A system is provided according to an aspect of the present application. The system may include: an image obtaining module, an image segmentation module, a texture model association module, and an output image generation module. The image obtaining unit may obtain an image. The image may include at least one pixel or voxel. The image segmentation unit may perform an image segmentation operation on the image to obtain a local image. The texture model association unit may associate the local image with a texture model. The texture model may determine an output color of the pixel or voxel of the associated local image based on the original color of the pixel or voxel. The output image generation module may determine an output color of the at least one pixel or voxel of the associated local image based on the texture model. The output image generation module may also generate an output image based on the output color.

In some embodiments, the system may further include a visualization device. The visualization device may display an interface. The interface may be configured to display the output image.

In some embodiments, the system may further include an operation device. The interface may include at least one interface element. The interface element may correspond to at least one texture model. The interface element may exemplarily present a display effect of the corresponding texture model. The operation device may be configured to operate on one of the at least one interface element for associating the texture model corresponding to the interface element with the local image.

In some embodiments, the system may further include an image recognition module. The image recognition module may be configured to identify a category of an object represented by the local image. The interface may display the at least one interface element based on the category of the object.

In some embodiments, the image segmentation module may be configured to obtain a plurality of local images by segmenting the image. The operation device may be configured to operate on different interface elements and associate a same or different texture models with each of the local images.

A system is provided according to another aspect of the present application. The system may include a data obtaining device. The data obtaining device may be configured to obtain a data set. The system may further include a storage, a processor, and instructions. The instructions may be stored in the storage. After the instructions are executed by the processor, the operations performed by the system may include one or more of the following operations. Obtaining an image. The image may include at least one pixel or voxel. Obtaining a texture model. Associating the image with the texture model. Determining an output color of the at least one pixel or voxel based on the texture model associated with the image. Generating an output image based on the output color of the at least one pixel or voxel.

A method is provided according to another aspect of the present application. The method may be implemented on at least one device, and each of the at least one device may have at least one processor and one storage. The method may include one or more of the following operations. Obtaining an image. The image may include at least one pixel or voxel. Obtaining a texture model. Associating the image and the texture model. Determining an output color of the at least one pixel or voxel based on the texture model associated with the image. Obtaining an output image based on the output color of the at least one pixel or voxel.

In some embodiments, the obtaining the texture model may include selecting the texture model from at least one texture model.

In some embodiments, the texture model may include at least one color parameter. The method may further include determining an output color of the at least one pixel or voxel of the image based on the color parameter.

In some embodiments, the method may further include one or more of the following operations. Displaying the image via an interface. Displaying the at least one texture model on the interface in the form of at least one interface element. An interface element of the at least one interface element may correspond to a texture model of the at least one texture model.

In some embodiments, the associating the image with the texture model may include one or more of the following operations. Displaying the image in a first region of the interface. Displaying the interface element corresponding to the texture model in a second region of the interface.

Performing, between the first region and the second region, a directional operation in a direction from the second region to the first region.

In some embodiments, the associating the image with the texture model may include one or more of the following operations. Displaying the image in a first region of the interface. Selecting the image. Displaying the interface element corresponding to the texture model in a second region of the interface. Selecting the interface element.

A method implemented on at least one device is provided according to another aspect of the present application. Each of the at least one device may have at least one processor and one storage. The method may include one or more of the following operations. Obtaining an image. Obtaining a local image based on the image. The local image may be a part of the image. The local image may include at least one pixel or voxel. Obtaining a texture model. Associating the local image with the texture model. Determining an output color of the at least one pixel or voxel of the local image based on the texture model associated with the local image. Generating an output image based on the output color of the at least one pixel or voxel.

In some embodiments, the obtaining the texture model may include selecting the texture model from at least one texture model.

In some embodiments, the method may further include one or more operations. Displaying the local image via an interface. Displaying the at least one texture model on the interface in the form of at least one interface element. An interface element of the at least one interface element may correspond to a texture model of the at least one texture model.

In some embodiments, the texture model may include at least one color parameter. The method may further include determining an output color of the at least one pixel or voxel of the local image based on the color parameter.

In some embodiments, the method may further include performing a segmentation on the image based on a segmentation algorithm to acquire the local image.

In some embodiments, the local image may represent an object. The method may further include determining a category of the object based on the segmentation algorithm.

In some embodiments, the obtaining the texture model may include selecting the texture model from at least one texture model according to the category of the object.

In some embodiments, the local image may represent an object. The method may further include identifying a category of the object.

In some embodiments, the identifying the category of the object may include matching the local image with a standard image. The method may further include determining the category of the object based on the matching result.

In some embodiments, one or more of the following operations may be further included. Obtaining a first local image based on the image. Obtaining a second local image based on the image. Selecting a first texture model from the at least one texture model. Associating the first texture model with the first local image. Selecting a second texture model from the at least one texture model. Associating the second texture model with the second local image. Determining the color of at least one pixel or voxel of the first local image based on the first texture model and generating a first output image therefrom. Determining the color of at least one pixel or voxel of the second local image based on the second texture model and generating a second output image therefrom. Generating a third output image based on the image. The third output image may include the first output image and the second output image.

In some embodiments, the first texture model and the second texture model may be the same texture mode. The first texture model or the second texture model may be edited. The colors of the pixels or voxels of the first output image and the second output image may change in accordance with the editing.

BRIEF DESCRIPTION OF THE DRAWINGS

The drawings, which are hereby incorporated by reference, provide a further understanding of the present application and form a part of this application. The illustrative embodiments of the present application and description thereof are intended to be illustrative of the present application and not intended to limit the present application. In the drawings, like reference numerals represent similar parts.

FIG. 2-A illustrates an architecture of a computing device according to some embodiments of the present application;

FIG. 2-B illustrates an architecture of a mobile device according to some embodiments of the present application;

FIG. 3-A illustrates a schematic diagram of an image processing system according to some embodiments of the present application;

FIG. 3-B is a flowchart illustrating an exemplary process of image processing according to some embodiments of the present application;

FIG. 4-A illustrates a schematic diagram of an image processing module according to some embodiments of the present application;

FIG. 4-B is a flowchart illustrating an exemplary process of image processing according to some embodiments of the present application;

FIG. 7-A illustrates a schematic diagram of an interface according to some embodiments of the present application;

FIG. 7-B illustrates a schematic diagram of a texture ball interface and a texture ball according to some embodiments of the present application;

FIGS. 8-A to 8-E illustrate schematic diagrams of the representations of the texture ball interface on the interface according to some embodiments of the present application;

FIGS. 9-A to 9-D are flowcharts and schematic diagrams illustrating exemplary process of associating operations between a texture ball and an image on an interface according to some embodiments of the present application;

FIG. 10-A is a flowchart illustrating an exemplary process of associating a local image with a texture model according to some embodiments of the present application;

FIGS. 10-B and 10-C illustrate schematic diagrams of associating at least one texture ball with a plurality of local images on an interface according to some embodiments of the present application.

DETAILED DESCRIPTION

Figure 1:
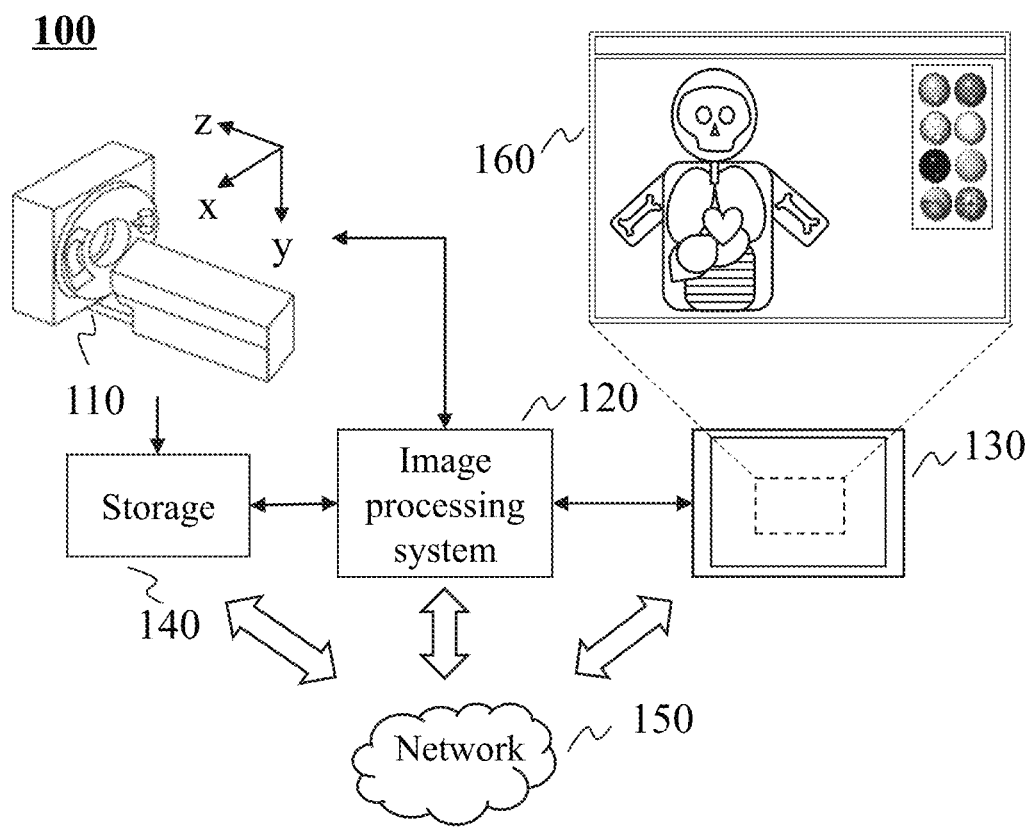
FIG. 1 illustrates a schematic diagram of an imaging system according to some embodiments of the present application.

In the field of computer graphics, adjustments of various parameters such as color tables are essentially matters of adjusting texture properties of an object, including the color and transparency of the texture itself, and various response properties of the texture to the ambient light. The present application may transform a list of color table adjustment parameters into one or more preset texture models that may be displayed to a user in the form of visual presentation in a user interaction interface (e.g., through a texture ball) to facilitate the selection for the user. The present application also proposes a new interactive manner. The user may determine a region of the image according to various algorithms or interactive manners. The user may select one texture model from a plurality of texture models. The user may associate the texture model with the region through a simple and intuitive interactive manner. The association may achieve an effect of emphasizing and distinguishing different local regions using textures described by different texture models. The user may also adjust a display manner and a display effect of at least one region associated with a texture model by adjusting property parameters of the texture model. The technical scheme disclosed in the present application may adjust local regions of a global image individually (e.g., an emphasis display, a blurring display, a highlight display, a boundary and contour enhancing display). The technical scheme disclosed in the present application may give the user simple and flexible interaction experience and optimize the display effect of the image.

The drawings will be briefly described below, so that the technical scheme of the embodiments of the present application can be illustrated more clearly. It should be understood that the drawings are merely examples or embodiments of the present application, and one of ordinary skills in the art may apply the present application to other similar situations according to these drawings without making creative efforts. Unless it is obvious in the language environment or otherwise indicated, the same reference numerals represent the same structure or operation.

In the present application and claims, the singular forms "a," "an," and "the" include plural referents unless the content clearly dictates otherwise. It will be further understood that the terms "comprises," "comprising," "includes," and/or "including" when used in the disclosure, specify the presence of stated steps and elements, but do not preclude the presence or addition of one or more other steps and elements. The present application may provide various illustrations of certain modules in an exemplary system, but the modules are merely illustrative. The system and method may use different modules in different application scenarios.

The operations performed by the system according to the embodiments of the present application are described using flowcharts in the present application. It should be understood that the operations in the flowcharts are not necessarily performed exactly in the order of examples thereof. Some or all of the operations in the flowcharts may be processed in some application scenarios simultaneously or reversely. In some application scenarios, one or more steps may be added or removed from the flowcharts.

Embodiments of the present application may be applied to color adjustments of medical three-dimensional images or two-dimensional images, such as color adjustments of CT (computed tomography) images and MRI images. It should be understood that the application scenarios of the system and method of the present application are merely examples or embodiments of the present application, and one of ordinary skills in the art may apply the present application to other types of medical three-dimensional images or two-dimensional images without making creative efforts. In addition, the present application may also be applied to non-medical fields such as animation, film, television, games, meteorology, archaeology, geological prospecting, public safety, and other fields relating to processing of three-dimensional images or two-dimensional images.

It should be noted that the following descriptions of the image color adjustment system are for convenience of description only, and not intended to limit the present application within the scope of the illustrated embodiments. It should be understood that after understanding the principles of the system, one of ordinary skills in the art may, without departing from this principle, make any combination of the modules, or connect constituent subsystems thereof with other modules, or make various modifications and variations in the form and details of the application of the method and system.

The image in the present application may represent a picture displayed in a visualization device, a pattern shown on a display medium, or an image data set corresponding to the picture or pattern. The image may be a two-dimensional image, a three-dimensional image, a four-dimensional image, or images of other dimensions. For convenience of description, the present application may take two-dimensional images and three-dimensional images as examples for introducing the image, and the introduction or description may also be extended to images of other dimensions. The image in the present application may be a bitmap image or vector image. An image element may be used to express a basic display unit in an image or a picture, or a basic data unit of image data. Image elements in the bitmap may be points or point data, in which an image element in a two-dimensional bitmap image may be a pixel. A basic image element of a three-dimensional bitmap image may be a voxel. An image element of a vector image may be an object. In the present application, for convenience of description, an image will be described by taking a two-dimensional bitmap or three-dimensional bitmap as an example, and the present application will be described by taking a pixel/voxel as a representative image element, but this does not limit the type of the image or the type of the image element.

The pixel/voxel may include a variety of parameters when used to represent a basic image data unit. For example, the pixel/voxel may include a coordinate parameter for determining a spatial position where a local object or picture of two-dimension or three-dimension represented by the pixel/voxel is located in the entire object or picture of two-dimension or three-dimension. The pixel/voxel may include color information for determining the color of the pixel/voxel displayed in a two-dimensional image or a three-dimensional image. The pixel/voxel may include transparency information for determining the degree of transparency of the pixel/voxel, that is, for determining a display effect of other pixels/voxels covered by the pixel/voxel in a particular view. The pixel/voxel may include reflection information for determining the influence of the display effect of other pixels/voxels located on a same optical path on the pixel/voxel. The pixel/voxel may further include other types of information.

In the present application, the texture may be related to the display effect of the image. Display properties used to describe the texture may include one or more of a color, a perspective effect, a reflection effect, or the like. In the present application, the color may include properties representing the display effect of the image itself such as grayscale, brightness, contrast, saturation and hue. The perspective effect and reflection effect may include properties capable of indicating an influence degree of the color of a local region in the image affected by the color of other images or other regions in the image, such as transparency, refractivity, reflectivity, shiness, ambient light, diffuse light, a specular effect and a specular scattering coefficient. Therefore, the term "texture" may be understood as a property that affects an overall display effect or a color effect of an image in different environments.

FIG. 1 illustrates a schematic diagram of an imaging system according to some embodiments of the present application. The imaging system 100 may include an information collection device 110, an image processing system 120, a human interface device 130, a storage 140, a network 150, and a user interface 160.

Different components/parts in the imaging system 100 may communicate with each other. For example, the image processing system 120 may interconnect or communicate with the network 150, or directly interconnect or communicate with the imaging system 100 or a part thereof (e.g., the information collection device 110, human interface device 130, or the like, or a combination thereof). For example, the image processing system 120 may send a processed image and/or data to the human interface device 130, obtain at least one user instruction from the human interface device 130, send at least one control instruction to the information collection device 110, and exchange data with storage 140, or the like. Data communication between the information collection device 110, the image processing system 120, the storage 140, the human interface device 130, as well as other devices that may be included in the imaging system 100 may be achieved by a data line, the network 150, or the like, or a combination thereof.

The information collection device 110 may scan a target object and acquire related data (e.g., scan data). The information collection device 110 may be a data obtaining device. The data obtaining device may be used to obtain and collect data related to the object. The information collection device 110 may refer to a device, or a device group. In some embodiments, the information collection device 110 may be a medical information collection device, such as a positron emission tomography (PET) device, a single-photon emission computed tomography (SPECT) device, a computed tomography (CT) device and a magnetic resonance imaging (MRI) device. These devices may be used individually or in combination. The information collection device 110 may be a PET-CT device, a PET-MRI device, a SPECT-MRI device, or the like. The scan data may be CT scan data, MRI scan data, ultrasound scan data, X-ray scan data, or the like, or a combination thereof.

The information collection device 110 may include a scanning component to scan the target object. The scanning component may be a radioactive scanning device. The radioactive scanning device may include a radioactive source. The radioactive source may emit radioactive rays to the target object. The radioactive rays may include microparticle rays, photon rays, or the like, or a combination thereof. The microparticle rays may include neutrons, protons, alpha rays, electrons, p media, heavy ions, or the like, or a combination thereof. The photon rays may include X-rays, y-rays, ultraviolet rays, lasers, or the like, or a combination thereof. For example, the photon rays may be X-rays. Accordingly, the information collection device 110 may be a CT system, a digital radiography system (DR), a multimodal medical imaging system, or the like, or a combination thereof. The multimodal medical imaging system may include a CT-PET system, a SPECT-MRI system, or the like, or a combination thereof. The information collection device 110 may also include a ray detection unit (not shown in FIG. 1) to accomplish the detection of the generated rays.

The image processing system 120 may generate an image based on the obtained data. For example, the image processing system 120 may generate an image based on the scan data. The scan data may be obtained from the information collection device 110 or the storage 140. The generated image may include information of the scanned object. The operation of generating the image based on the scan data may include one or more operations of data stacking, Fourier transform, transforming signal intensity into a grayscale value, three-dimensional reconstruction, multimodal fusion, or the like. The generated image may be a two-dimensional image (e.g., a slice image), a three-dimensional reconstructed image, a four-dimensional reconstructed image, a multimodal image, or the like. The generated image may be a grayscale image, a black and white image, a binary image, a full-color image, or the like. During a process of generating the image based on the scan data, the image processing system 120 may further perform one or more data processing operations such as data preprocessing, data transformation processing, data cleaning processing, data fitting processing, and/or data weighting processing, or the like, or a combination thereof.

In some embodiments, the image processing system 120 may process the scan data and generate at least one image based on the data. The scan data may be the same type of scan data or different types of scan data. For example, the image processing system 120 may process MRI scan data and CT scan data, and generate a corresponding MRI scan image and a CT scan image based on the two different types of scan data. The scan data may be obtained from a same or different types of information collection device 110, human interface device 130, storage 140, and/or network 150, or the like. The generated images may be of a same type or different types. The scan image may be a CT image, an MRI image, an ultrasound image, an X-ray image, or the like, or a combination thereof. In some embodiments, the image processing system 120 may perform operations such as image registration and/or image fusion on a plurality sets of scan data or scan images to generate at least one fusion image.

The image processing system 120 may further process the image. In some embodiments, the image processing system 120 may process the generated image with one or more operations including image segmentation, selection of region of interest, image registration, image recognition, and addition of display color, etc.

In some embodiments, the image processing system 120 may generate a medical three-dimensional image (e.g., an MRI or CT image) based on scan data of a human body (e.g., MRI data or CT data). The image processing system 120 may perform image segmentation on the medical three-dimensional image to obtain at least one local image representing different tissues or organs of the human body. The image processing system 120 may add different textures to each local image.

The image processing system 120 may generate an output image based on the scan image. The output image may be displayed on the user interface 160 or the human interface device 130. In some embodiments, the image processing system 120 may adjust the output image based on the operations performed by the user on the user interface 160, such as scaling, rotating, changing display effects (e.g., colors or lighting effects) and changing display regions.

The image processing system 120 may use one or more algorithms to process the data or images. For example, the one or more algorithms may include Fourier transform, a fitting algorithm, a filtered backprojection, an iterative algorithm, histogram expansion calculation, image data function optimization, a level set algorithm, an image segmentation algorithm, a neural network algorithm, or the like, or a combination thereof.

In some embodiments, the image processing system 120 may control the information collection device 110. The control instruction for controlling the information collection device 110 may be generated through a calculation by the image processing system 120, or generated according to information (e.g., a user instruction) obtained from other devices (e.g., the human interface device 130). In some embodiments, the image processing system 120 may generate the control instruction according to at least one user instruction. For example, the control instruction may be an adjustment of at least one imaging parameter of the information collection device 110. The imaging parameters may include at least one of the scan time, the location information of the scan target, the rotation speed of a gantry, a scan parameter, or the like. The information collection device 110 may obtain data according to the control instructions. In some embodiments, the image processing system 120 may adjust an algorithm or a parameter of the algorithm used during the data processing or image processing according to the user instructions.

In some embodiments, the image processing system 120 may store data in the storage 140 or retrieve data from the storage 140. The data may be data directly or indirectly obtained from the information collection device 110, temporary data or non-temporary data generated by the image processing system 120 itself, or data for assisting the image processing system 120 in performing image processing, or the like.

In some embodiments, the image processing system 120 may be one or a set of computers. The set of computers for constituting the image processing system 120 may be in wired or wireless connection (for example, through the network 150). A set of computers for constituting the image processing system 120 may indirectly communicate through at least one device. The image processing system 120 may be installed at the same geographic location together with the information collection device 110. The image processing system 120 may be implemented on a cloud. In some embodiments, the image processing system 120 may be a part of the information collection device 110. The human interface device 130 may be a component of the information collection device 110 or an independent device.

The human interface device 130 may provide information for the user or receive information from the user. The human interface device 130 may include at least one output component and at least one input component (not shown in FIG. 1), or the like. The output component may be used to provide the information for the user. The input component may be used to receive the information from the user. The human interface device 130 may be an independent device having a certain computing capability or data processing capability, such as a desktop computer, a laptop, a tablet computer, a mobile phone, a television and a wearable device. The human interface device 130 may be at least one component attached to the image processing system 120, such as a display, a mouse, a keyboard, a touch screen, a joystick and a remote control.

The information provided by the human interface device 130 for the user may include at least one of a program, software, an algorithm, data, a signal, a text, an image, audio, or the like, or a combination thereof. The human interface device 130 may provide the information for the user in the form of video, audio, neural signal, physical contact, alarm, or the like, or a combination thereof. The provided information may be obtained from the human interface device 130, the image processing system 120, the information collection device 110 and/or other possible devices/components in the imaging system 100. The human interface device 130 may provide the information for the user through at least one of the output components. The output components may be a data output port (e.g., a USB interface), a visualization device (e.g., a display), an audio component (e.g., a loudspeaker), a signal indicator, an electrode, a sensor, or the like.

The visualization device may be used to present at least one image to the user. The image data from the image processing system 120 and image information generated by the human interface device 130 itself may be visually presented to the user by at least one visualization device. The manner of visual presentation may be image display, printing, projection, or the like. The visualization device may be an independent device (e.g., a display, a television, a projector, a printer) or a component with a display function in an independent device (e.g., a screen of a mobile phone, a laptop, or a tablet computer). The visualization device may use at least one flat panel display as a display medium when visually presenting an image in a manner of image display. The visualization device may use a projection screen, a holographic film, a holographic plate, a wall, a floor, an exhibition board, a water curtain, smoke, air, an electromagnetic field, or the like, or a combination thereof, as a display medium when visually presenting an image in the manner of projection. The visualization device may use a printing mode such as two-dimensional printing (e.g., inkjet printing, laser printing, ink printing), three-dimensional printing, or the like, or a combination thereof when visually presenting an image in the manner of printing.

The visualization device may be a two-dimensional visualization device (display an image in a two-dimensional display manner) or a three-dimensional visualization device (display an image in a three-dimensional display manner), or the like. A two-dimensional image may be directly displayed through a two-dimensional visualization device or a three-dimensional visualization device. A three-dimensional image may be directly displayed through a three-dimensional visualization device, or displayed in simulation through a two-dimensional visualization device. When a three-dimensional image is displayed through a two-dimensional display, information for an observation position and/or an observation direction may be provided, and then the three-dimensional image may be transformed into a two-dimensional output image using a rendering technique. The two-dimensional output image may simulate a three-dimensional display effect of the three-dimensional image through a two-dimensional display. The rendering technique may use a section or a projection of the three-dimensional image as the two-dimensional output image according to the observation position and/or the observation direction. The rendering technique may be a volume rendering technique. The volume rendering technique may use a variety of algorithms, such as a ray casting algorithm, a splatting algorithm, a shear warp algorithm and a three-dimensional texture mapping algorithm. The rendering technique may further change color information of pixels in the two-dimensional output image and simulate a 3D display effect, such as adding a lighting effect, depth of field or a blur effect. Different two-dimensional output images may be generated based on the three-dimensional image by setting different observation positions and/or observation directions. The external structure and/or internal structure of the three-dimensional image may be illustrated through the series of two-dimensional output images.

It should be noted that a three-dimensional image processed by rendering may be a two-dimensional image simulating a three-dimensional display effect. For convenience of description, where "presenting" or "displaying" a three-dimensional image is related in the present application, the term "three-dimensional image" may still be used to describe an image obtained after an operation of "presenting" or "displaying", even if the image obtained is actually a two-dimensional image. For a basic image unit of the image obtained after "presenting" or "displaying", even if it may actually be a pixel, the term "voxel" may still be used to describe the pixel in the present application. The "voxel" may represent a voxel corresponding to the pixel in the three-dimensional image being "presented" or "displayed". When the visualization device needs to display an image of a higher dimension (e.g., a four-dimensional image), a display manner thereof may be outputting a two-dimensional image or a three-dimensional image that changes over time.

The information received by the human interface device 130 from the user may include user operation data or user input data, or the like. The user operation data may be used to operate at least one component of the imaging system 100. The user input data may be used to process data/images of the image processing system 120 or analyze processing results. The user operation data or user input data may include at least one of a program, software, an algorithm, data, a sensing signal, a text, an image, video, audio, or the like, or a combination thereof. The user input data may include scan data, a scan image, an output image, temporary data/images, algorithm/model data, parameter data, reference data/image, or the like. The temporary data/images may be at least one dataset/image generated during a process of generating a scan image based on the scan data, or a process of generating an output image based on the scan image. The algorithm/model data may be a specific code used by the image processing system 120 for implementing at least one algorithm/model (e.g., different types of image segmentation algorithms, texture models). The parameter data may be at least one parameter input into an algorithm or model when the image processing system 120 uses the algorithm or model. The reference data/images may be at least one standard data/image referenced by the image processing system 120 or the user references during data or image comparison (e.g., during processing of system calibration, image recognition, image registration, lesion analysis, disease diagnosis). The user input data may also be a program code for implementing at least one function implementing the imaging system 100.

The human interface device 130 may receive the user operation data, user input data, or the like, from the user through the input component. The input component may include at least one of a keyboard, a touch device, a mouse, a key, an audio input device (e.g., a microphone), an image input device (e.g., a scanner, a camera), a remote control device (e.g., a remote control, a remotely connected computer), a data input device (e.g., a CD driver, a USB port), or the like. The manner in which the user inputs the user operation data or user input data via the input device may include, but not limited to, a mouse operation, a keyboard input, a key operation, a touch control, a voice control, a gesture operation, an expression operation, a motion sensing operation, a neural signal operation, or the like, or a combination thereof. In some embodiments, the user may input, directly or indirectly, through the input device, input information such as instrument parameters, data processing parameters, image processing parameters and image display parameters into the human interface device 130, image processing system 120, information collection device 110 and/or other possible devices/components in the imaging system 100. The input information may be obtained from an external data source (e.g., a floppy disk, a disk, a disc, a memory chip, the network 150).

The storage 140 may be used to store data. The data may be data generated or obtained by the imaging system 100, such as scan data, data generated during the running of least one component of the imaging system 100, data input by the user through the human interface device 130 and data obtained by the user through the network 150 from data sources (not shown in FIG. 1). The storage 140 may be a device/component or a combination of several devices/components with a storage function. In some embodiments, the storage 140 may include at least one independent device with a data storage function, such as a computer or a server. The storage 140 may include a local storage or a remote storage (e.g., a cloud storage implemented on the network 150). In some embodiments, the storage 140 may include a component with the data storage function in an independent device, such as a disk or a disk array. The storage 140 may include a component with the storage function of any device (e.g., the information collection device 110, the image processing system 120, the human interface device 130) of the imaging system 100.

In some embodiments, the storage 140 may store the scan data. The scan data may be obtained from the information collection device 110, the human interface device 130 (for example, obtained through a socket of a mobile storage device), the network 150, or the like. For example, the storage 140 may store CT scan data and/or MRI scan data, or the like. In some embodiments, the storage 140 may store temporary data/images or non-temporary data/images generated when the image processing system 120 and/or the human interface device 130 is normally running. For example, the storage 140 may store some system running temporary files, scan images, output images, temporary data/images, or the like. In some embodiments, the storage 140 may store information collected by the human interface device 130 from the user, or data generated based on the information, such as user operation data, user input data, user instructions and authentication data.

In some embodiments, the storage 140 may store program codes (e.g., a software, an operating system) for running the information collection device 110, the image processing system 120 and/or the human interface device 130. The storage 140 may also store at least one algorithm/model data, parameter data, reference data/images, or the like. The program code, algorithm/model data, parameter data, standard data or the like may be added, by an installation program, when a program for implementing at least one function of the imaging system 100 is installed, or be added by the user via the human interface device 130 or the network 150, to the storage 140.

In some embodiments, the network 150 may be used to transmit information between each device/component in the imaging system 100. In some embodiments, the network 150 may be used by the imaging system 100 to obtain information from a remote server. The network 150 may be an independent network or a combination of different networks. For example, the network 150 may include a local area network (LAN), a wide area network (WAN), a public switched telephone network (PSTN), a virtual network (VN), or a combination thereof. The network 150 may include a plurality of network access points. The network 150 may use a wired network architecture, a wireless network architecture, and a wired/wireless network hybrid architecture. The wired network may include a metal cable, a hybrid cable, an optical cable, or the like, or a combination thereof. Transmission manners of the wireless network may include Bluetooth, Wi-Fi, ZigBee, near field communication (NFC), cellular networks (including GSM, CDMA, 3G, 4G), or the like.

The user interface 160 may be used to graphically present a plurality of information in the imaging system 100 to the user. The user interface 160 may be displayed through the at least one visualization device of the human interface device 130. The user interface 160 may be generated through an application program. The application program may be a computer program, a mobile device application (e.g., a mobile phone APP), or the like. In some embodiments, the application program may be executed by the image processing system 120 and configured to implement one or more functions of the image processing system 120. In some embodiments, the application program may be run on the human interface device 130 and configured to remotely control the image processing system 120. The application program may be stored in the storage 140. The storage 140 may be a component with the storage function in the image processing system 120 or the human interface device 130.

The user interface 160 may include at least one graphical interface element. The interface element may have a visual effect, such as a pattern, a text, or a combination thereof. The visual effect of the interface element may be preset or generated in real time. The interface element may be used to display at least one piece of information, for example, an image generated by the image processing system 120, a text or graphic description of outcomes of graphic analysis or data processing, a text or graphic description representing working conditions of each component or device of the imaging system 100, or the like. In some embodiments, the user interface 160 may display phased information of an imaging process and/or image processing/analysis outcomes to the user, such as, an image generated based on the scan data, an image (or mask) obtained through image segmentation, an image selected by the user, a texture-added image, at least one standard image, a result of image registration, a result of image recognition, or the like.

The interface element may be used to assist the user in operating the imaging system 100, or provide one or more operation modes for the user. For example, the interface element may include a pointer, a cursor, a set of grid lines, a button, a menu, a scroll bar, a text box, or the like. The user operation data input by the user through the human interface device 130 may affect the interface element. For example, the user may press (or click) a button on the user interface 160 through the mouse, or input a parameter or a piece of code into a text box of the user interface 160 through the keyboard. The term "interface operation" may be used to represent a process that the user inputs the user operation data and thereby affecting at least one interface element. The interface operation of the user may be transformed, through at least one module of the application program, into a command, i.e., the user instruction, that may be executed by at least one device/component (e.g., the image processing system 120, or the information collection device 110) of the imaging system 100.

The user may operate at least one device/component of the imaging system 100 through the user instruction, such as initializing/maintaining the information collection device 110, storing/retrieving data in/from the storage 140, turning on/off the image processing system 120, and connecting/disconnecting the network 150, etc. The user may also initialize or call one or more functional module of the image processing system 120 through the user instruction. In some embodiments, the user may command the image processing system 120, through the at least one user instruction, to perform one or a series of operations, such as generating a scan image, segmenting an image, recognizing an image, associating an image with a texture model as well as generating an output image.

The interface element may provide at least one operation plan for the user. The operation plan may include one or more combinations of one/a series of algorithms, one/a set of parameters, or the like. In some embodiments, the user interface 160 may provide a series of interface elements with different display effects when the user needs to segment an image. These interface elements may represent different segmentation approaches separately, such as a vessel segmentation approach, a bone segmentation approach and a liver segmentation approach. The user may perform the interface operation on one or more of these interface elements so as to perform one or more segmentation approaches corresponding to these interface elements. In some embodiments, the user interface 160 may provide a series of interface elements (e.g., a texture ball 750) representing different texture models when the user needs to associate an image with a texture model. These interface elements may have the same or similar display effect as the texture models represented by the interface elements to facilitate the selection of the user. The user may perform an interface operation (e.g., dragging) on one of the interface elements so as to apply a texture model corresponding to the interface element to an image.

In the imaging system 100, devices/components may be directly connected with each other, or indirectly connected through at least one switching device/component (not shown in FIG. 1). For example, the information collection device 110, the image processing system 120, the human interface device 130, and the storage 140 may be directly or indirectly connected with each other. The switching device/component may be an entity (e.g., a filter, a router, a server, a set of signal transceivers) or a non-entity (e.g., radio waves, light waves, sound waves, electromagnetic waves, or the like, or a combination thereof). Different devices/components may be in wired and/or wireless connection. In some embodiments, the information collection device 110, the image processing system 120, the human interface device 130, and the storage 140 may communicate date through the network 150.

In some embodiments, the information collection device 110, the image processing system 120 and the human interface device 130 may be a data obtaining device. The data obtaining device may be used to obtain image data and/or texture models, or the like. For example, the image processing system 120 may be a computer, and the computer may obtain image data and texture models to process an image.

It should be noted that the above descriptions of the imaging system 100 are for convenience of description only, and not intended to limit the present application within the scope of the illustrated embodiments. It should be understood that, for a person having ordinary skills in the art, after understanding the principles of the system, a variety of changes may be made to the imaging system 100 in detail. For example, combining a plurality of devices/components/modules arbitrarily (e.g., combining the image processing system 120, the storage 140, and the human interface device 130 into one device), splitting a single device/component/module (e.g., splitting the image processing system 120 into one or more devices for performing at least one function of the image processing system 120 separately), adding a device/component (e.g., a filter device) not related to the present application into the imaging system 100, changing the connection manner between the main devices/components from direct connection to indirect connection (e.g., adding at least one signal transceiver, transcoding device), changing the type of the information collection device 110 so as to apply the imaging system 100 to other fields, or the like. However, these changes will not depart from the scope of protection of the claims.

FIG. 2-a illustrates an architecture of a computing device according to some embodiments of the present application. A computer 200 may be applied to the imaging system 100, any device/component (e.g., image processing system 120, human interface device 130) included in the imaging system 100, functional modules included in the devices/components (e.g., data processing module 320, image processing module 340), function units included in the functional modules (e.g., image segmentation unit 420, image recognition unit 430), or the like, so as to implement one or more functions of the system, devices, components, modules, or units, etc., in the present application. The computer 200 may implement at least one function of the imaging system 100 (e.g., image segmentation, texture model association) through a hardware device, a software program, firmware, or a combination thereof. The computer 200 may have a general application scenario or a particular application scenario (e.g., for generating, processing, or displaying a medical image). The computer 200 may be one or a set of computers. For convenience, only one computer 200 is depicted in FIG. 2-a, but any function (e.g., scan data collecting, data processing, image processing) of the imaging system 100 described in this application may be implemented by a set of similar computer platforms in a distributed manner (in parallel or in serial) to decentralize a processing load of the imaging system 100.

The computer 200 may include an internal communication bus 201, a processor 205, a data storage unit (e.g., read-only memory (ROM) 206, a random access memory (RAM) 207, a disk 208), an input/output component (I/O) 209, a network interface card (NIC) 211, or the like. The internal communication bus 201 may be used to transmit data between different components in the computer 200. The processor 205 may be used to perform at least one instruction (including the user instruction, a program instruction, the control instruction) or an operation of at least one algorithm (e.g., an image segmentation algorithm). The processor 205 may include a chip or a chipset. One or more functions of the image processing system 120 may be implemented by the processor 205. The computer 200 may further include a graphics processing unit (GPU, not shown in FIG. 2-a for assisting the processor 205 in processing graphic data. The graphics processing unit may be an independent component in the computer 200 or may be integrated on the same chip with the processor 205.

The ROM 206, the RAM 207, the disk 208 may store various data files or programs (detailed descriptions may be found in relevant descriptions of the storage 140 illustrated in FIG. 1) in the computer operations, computer communications, and implementation of computer functions, or the like. The I/O component 209 may support the data communication of computer 200 with at least one peripheral device 213. The I/O component 209 may include at least one connection port, such as a communication port (COM), a universal serial bus (USB) port, a high-definition multimedia interface (HDMI) port, a video graphics array (VGA) port, a digital video interactive (DVI) port and a PS/2 port. The peripheral device 213 may perform data communication through the I/O component 209 and the internal communication bus 201. The peripheral device 213 may be a device for inputting or outputting, such as a display, a printer, a mouse, a keyboard, a gamepad, a touch screen, a camera, a loudspeaker, or the like, or a combination thereof. The peripheral device 213 may include at least one input component and output component (more detailed descriptions may be found in relevant descriptions of the human interface device 130 illustrated in FIG. 1) in the human interface device 130. The NIC 211 may perform data communication through at least one network (more detailed descriptions may be found in relevant descriptions of the network 150 in illustrated in FIG. 1).

FIG. 2-b illustrates an architecture of a mobile device according to some embodiments of the present application. A mobile device 250 may be applied to the human interface device 130 or other possible devices/components included in the imaging system 100. The mobile device 250 may implement at least one function of the human interface device 130 (e.g., graphic display, receiving user operation information) through a hardware device, a software program, firmware, or a combination thereof. The mobile device 250 may be used to remotely operate the image processing system 120 and display image information output by the image processing system 120. The mobile device 250 may include a touch display screen 253, a key (e.g., key 255-1, 255-2, 255-3), an internal communication bus 260, a processing module 265, a data storage (e.g., read-only memory (ROM) 262, random access memory (RAM) 263), a connection port 268, a communication module 261, a display module 267, an input module 266, or the like. At least one module of the mobile device 250 as well as each component of the at least one module may be independent of each other or be integrated on a same chip. In some embodiments, the mobile device 250 may be a mobile phone, a tablet computer, a smart wearable device, or other devices with an image display function and a remote operation function.

The internal communication bus 260 may be used to transmit data between different components or modules in the mobile device 250. The processing module 265 may be used to perform at least one instruction (including the user instruction, the program instruction, the control instruction) or at least one algorithm (e.g., an image segmentation algorithm). The processing module 265 may include at least one application processor (AP), at least one baseband processor (BP), at least one graphics processing unit (GPU), at least one coprocessor, or the like, or a combination thereof. One or more functions of the human interface device 130 may be implemented by the at least one processor or processing unit of the processing module 265. A plurality of processors or processing units of the processing module 265 may exchange data through the internal communication bus 260 directly, or exchange data through the at least one data storage (e.g., RAM) indirectly.

The touchscreen 253 may be used to display image information and allow the user to operate based on the currently displayed image information. The touchscreen 253 may include a display screen and a touchpad. The display screen may be used to display image information output by the mobile device 250, such as user interface 160. The display screen may obtain graphic data for display through the display module 267. The touchpad may be used to receive a user touch-control operation and transform the touch-control operation into information such as coordinates, touch intensity, and touch duration. The user may also input operation information through at least one key (e.g., key 255-1, 255-2, 255-3). The operation information may be directly or indirectly transmitted, through the input module 266, to the processing module 265 and transformed into at least one user instruction. In some embodiments, the touchpad may be transparent and cover the surface of the display screen (as shown in FIG. 2-b). Therefore, the user may perform the touch-control operation on a region, corresponding to the at least one interface element displayed on the display screen, on the touchpad, so as to activate one or more functions corresponding to the interface element.

The ROM 262 and the RAM 263 may store various data files or programs (see relevant descriptions of the storage 140 illustrated in FIG. 1 for detailed information) during the processes, performed by the mobile device 250, of calculation, communication, implementing one or more functions. The connection port 268 may be used to connect the mobile device 250 with at least one device (e.g., a computer, another mobile device 250, an external infrared device, an external Bluetooth device, an external card reader device, an external camera, a headset, an adapter. Not shown in FIG. 2-b). The connection port 268 may include at least one of a micro-USB port, a USB Type-C port, a lightening port, an audio port, or the like.

The mobile device 250 may perform data exchange through the communication module 261 and the network 150. The communication module 261 may include at least one of a radio frequency communication module, a WI-FI module, a Bluetooth module, an NFC module, or the like. The detailed information of the network 150 may refer to relevant descriptions of FIG. 1.

The mobile device 250 may further include at least one audio device (not shown in FIG. 2-b) and an audio module 269. The audio device may include at least one of a loudspeaker, a microphone, or the like. The audio device may perform audio coding, audio decoding, etc., through the audio module 269. The audio device may exchange audio information through the audio module 269 with at least one module of the mobile device 250.

The mobile device 250 may further include at least one sensor (not shown in FIG. 2-b) and a sensor module 264. The sensor may include a gesture sensor, a motion sensor, a proximity sensor, a gyro sensor, an acceleration sensor, a geomagnetic sensor, a pressure sensor, a grip sensor, a temperature/humidity sensor, an infrared sensor, or the like, or a combination thereof. The sensor may generate corresponding sensing information and transmit the corresponding sensing information to at least one module of the mobile device 250 through the sensor module 264. Some of the sensing information (e.g., sensing information generated by the gesture sensor, the motion sensor, the gyro sensor or the acceleration sensor) may be used to generate user instructions.

FIG. 3-a illustrates a schematic diagram of an image processing system according to some embodiments of the present application. The image processing system 120 may include a data input/output module 310, a data processing module 320, an image processing module 340, and an interface module 360. The image processing system 120 may further include other modules (not shown in FIG. 3-a). The modules may be directly or indirectly connected with each other. The modules may be implemented by one or a set of devices (e.g., at least one processor 205, processing module 265, graphics processing unit). In some embodiments, a plurality of the modules may be implemented by the same device or the same set of devices.

The data input/output module 310 may be used to input or output data. The data for input or output may be scan data, algorithm/model data, parameter data, scan images, output images, temporary data/images, reference data/images, user instructions, etc. Relevant information of the data may refer to relevant descriptions in FIG. 1. The input/output module 310 may communicate data with at least one module in the image processing system 120, such as the data processing module 320 and the image processing module 340. The input/output module 310 may perform data communication with at least one device in the imaging system 100, such as the information collection device 110, the human interface device 130, and the storage 140.

In some specific embodiments, the data processing module 320 may obtain the scan data from the information collection device 110 or the storage 140 through the input/output module 310. The image processing module 340 may send the output images to the human interface device 130 or the storage 140 through the input/output module 310. The data processing module 320 and the image processing module 340 may obtain user instructions from the human interface device 130 through the input/output module 310, or obtain algorithm/model data, reference data/images, parameter data, or the like from the storage 140.

The data processing module 320 may generate at least one scan image based on the scan data. The scan data may be obtained from the information collection device 110, the storage 140, the network 150, or the like through the data input/output module 310. The scan image may be a two-dimensional image, a three-dimensional image, a four-dimensional image, or the like. The scan image may be a grayscale image, a black and white image, a binary image, a full-color image, or the like.

In the present application, the grayscale image may have following features. Each pixel/voxel of the grayscale image may have colors belonging to a same color category. The color category may include two possible colors, and a series of transition colors between the two colors. The color category usually used by the grayscale image may be a gray category, that is, a series of grays between the darkest black and the brightest white. The series of grays may represent different levels of color depth (or brightness), and the depth (or brightness) level may be represented by grayscale. The grayscale image may be an 8-bit grayscale image (including 256-level grayscale), a 16-bit grayscale image (including 65536-level grayscale), or the like. The grayscale image may also use other color category, such as a green category (between the darkest black and the brightest green), a red category, a blue category and other user-defined color category (e.g., a series of colors between red and blue), and the specific color of each pixel/voxel is related to the grayscale thereof.

In some embodiments, the data processing module 320 may generate a grayscale image based on the scan data. The scan data may be a data matrix that describes the distribution of the signal intensity in a geometric space. The data processing module 320 may transform the data representing the signal intensity in the scan data into grayscale data by a grayscale function. In some embodiments, the grayscale function may transform the data with higher signal intensity into grayscale with lighter (or brighter) color depth, and transform the data with lower signal intensity into grayscale with deeper (or darker) color depth. The distribution of the signal intensity in geometric space may be transformed into distribution of grays with different color depth (or brightness) in the geometric space through the grayscale function, so that the scan data may be transformed into a grayscale scan image.

In some embodiments, the data processing module 320 may perform one or more steps of data processing on the scan data and then generate a grayscale image based on processing results. In some embodiments, the scan data does not describe the distribution of the signal intensity in the geometric space. For example, the scan data may be K-space data. The data processing module 320 may perform a data transformation operation (e.g., Fourier transform) on the scan data to generate processing data describing the distribution of the signal intensity in the geometric space, and then generate a scan image based on the processing result. In some embodiments, the scan data may be a plurality of incomplete scan data sets (e.g., MRI data, X-ray data, or the like, obtained by the partial parallel acquisition technique). Therefore, before data transformation, the data processing module 320 may need to generate at least one complete scan data based on the scan data set, and then generate a desired scan image via one or more operations.

In some embodiments, the data processing module 320 may further perform processing operations on the preliminarily generated scan image. In some embodiments, the preliminarily generated scan image may include at least one artifact or noise. The data processing module 320 may perform one or more steps of operations to remove artifacts or denoise the scan image. In some embodiments, the data processing module 320 may process a plurality of scan data from different sources, such as CT data, MRI data, ultrasound data and X-ray data, and generate one or more scan images of different types. The data processing module 320 may further generate at least one fused image based on the scan images. In some embodiments, the scan images generated by the data processing module 320 may be a set of two-dimensional images representing different sections of a three-dimensional object. The data processing module 320 may generate a three-dimensional image based on the set of two-dimensional images through a three-dimensional reconstruction operation for a next operation.

The image processing module 340 may process an image. The image may be an image generated by the data processing module 320 (e.g., the scan image) or an image obtained from other devices or components (e.g., the storage 140, the network 150) of the imaging system 100 by the input/output module 310. The processing processes may include operations of image selection, image segmentation, image recognition, texture model association, display effect adjustment, texture parameters editing or replacement, or the like, or a combination thereof. The image may be processed to generate an output image. The output image may be output through the input/output module 310, or stored in a storage module (not shown in FIG. 3) of the image processing system 120. The output image may be sent to the user interface 160 or the human interface device 130 for display.

In some embodiments, the image processing module 340 may select an image region based on an operation performed by the user on the user interface 160 or the human interface device 130. The selected image region may have a display effect different from that of other image regions on the user interface 160. The image processing module 340 may perform one or more image processing operations on the selected image region according to the user operation. The image processing module 340 may also perform one or more image processing operations on image regions other than the selected image region according to the user operation. The image processing module 340 may also have one or more image processing functions that are not affected by image selection.

In some embodiments, the image processing module 340 may perform one or more image segmentation operations on the scan image and generate at least one segmented image. For example, the scan image may be a CT image of lower limbs of a human body, and a lower limb vessel image may be obtained by performing a vessel segmentation operation. A lower limb bone image may be obtained by performing a bone segmentation operation.

In some embodiments, the image processing module 340 may identify a category of an object represented by at least one image. For example, the image processing module 340 may recognize an image having features of a liver as a liver, or identify an image region with abnormal grayscale (not caused by artifacts or other factors) as a tumor, a polyp, or the like. The at least one image may be a scan image, a segmented image obtained based on a scan image, other types of images input by a user, or the like. The image processing module 340 may adjust the display effect of at least one image (e.g., the scan image or the image generated based on the scan image) so as to show a distinction.

In some embodiments, the image processing module 340 may associate an image with a texture model, or edit at least one texture parameter in the texture model. The texture parameters may relate to color, brightness, contrast, transparency, a reflection effect, or the like. In some embodiments, the image may be a grayscale scan image generated by the data processing module 320. The image processing module 340 may generate a full-color image based on the grayscale scan image.

In the present application, each pixel/voxel of a full-color image may have combined colors belonging to different color categories. The full-color image may use different color systems to represent colors, such as RGB, HSL, CMYK, YIQ, YUV and YCbCr. Taking the RGB system as an example, the RGB system may include three color channels, red channel (R), green channel (G) and blue channel (B). Each color channel of the RGB system may be represented by grayscale. Grayscale levels (or color scale) of different color channels may represent "ratio" of red (R), green (G), or blue (B) when a color is generated or displayed. Colors of different "ratio" may be superimposed or mixed to generate or display a target color. Each color channel of the RGB system may use color scales with a same or different numbers of levels (or bits). The color scale of each color channel may have a property similar to the grayscale.

A specific color in the RGB system may be represented through a three-dimensional array, for example, (r, g, b), where r, g, b represent color scale levels of the color in the R channel, G channel, and B channel, respectively. Taking a 24-bit RGB system as an example, r, g, b, may be integers between 0 and 255, respectively. For the color scale of each channel, 0 may represent the darkest color, i.e., black. 255 may represent the brightest color of the channel (for example, the brightest color of the R channel is red). Different color scale levels of 0 to 255 may represent colors of different depth or different brightness between the darkest color and the brightest color. For example, in the 24-bit RGB system, RGB (0, 0, 0) may be a kind of black, RGB (255, 255, 255) may be a kind of white, RGB (125, 125, 125) may be a kind of gray, RGB (255, 0, 0) may be a kind of red, and RGB (0, 255, 255) may be a kind of yellow. The RGB system may further include an Alpha channel (A) to constitute an RGBA system. Grayscale in the Alpha channel may represent the transparency of a color. For example, RGBA (255, 0, 255, 0) may be used to represent a kind of opaque purple, and RGBA (255, 120, 0, 100) may be used to represent a kind of translucent orange. For convenience of description, the present application will be described by taking the RGBA color system as an example.

In some embodiments, the image processing module 340 may also include at least one unit. The type and specific function of the at least one unit may refer to relevant descriptions in FIG. 4.

The interface module 360 may transform an image into image data that may be displayed by a display device. The display device may be the user interface 160 or the human interface device 130. The image may be an image obtained after being processed by the image processing module 340. The image may be an image obtained from other devices or components (e.g., the storage 140) of the imaging system 100 through the input/output module 310.

In some embodiments, a program for generating the user interface 160 may run on the image processing system 120. The interface module 360 may be a part of the program. The interface module 360 may transform the user interface 160 and an image processed by the image processing system 120 into a data stream that may be displayed by the human interface device 130. The interface module 360 may transform an operation performed by the user on the at least one interface element of the user interface 160 into a user instruction, so as to operate the image processing system 120 and/or other devices/components in the imaging system 100.

In some embodiments, a program for generating the user interface 160 may run on the human interface device 130, and operate the image processing system 120 by remote communication. The interface module 360 may be a module independent of the program. The interface module 360 may transform an image processed by the image processing system 120 into data that may be recognized by the program. The interface module 360 may recognize and send the user instruction transmitted to the image processing system 120 by the program.

It should be noted that the above descriptions of the image processing system 120 are merely for convenience of description, and not intended to limit the present application within the scope of the illustrated embodiments. It should be understood that, for a person having ordinary skills in the art, after understanding the principles of the system, the components in the image processing system 120 may be arbitrarily combined, split, or changed in detail. For example, the data processing module 320 may be combined with the image processing module 340 into one module. The data processing module 320 and/or the image processing module 340 may also be split into at least one module. The image processing system 120 may be added with at least one additional module, such as a data noise reduction module. However, these changes will not depart from the scope of protection of the claims.

FIG. 3-b is a flowchart illustrating an exemplary process of image processing according to some embodiments of the present application. One or more operations of flow 300 may be performed by devices shown in FIGS. 2-a and/or 2-b.

In 370, scan data may be obtained. The obtaining of the scan data may be performed by the image processing system 120. In some embodiments, the image processing system 120 may obtain the scan data through the input/output module 310. The scan data may be one or more of MRI scan data, CT scan data, and/or X-ray scan data.

The scan data may be obtained, partially or all, from the information collection device 110, other devices or components (e.g., the storage 140) of the imaging system 100, or the like, or a combination thereof. For example, the scan data may be data obtained by performing a scanning on an object (e.g., human body) by the information collection device 110. As another example, the scan data may be data stored in the storage 140. As another example, the scan data may be partially obtained from the information collection device 110, and partially obtained from the storage 140.

The scan data may be obtained directly or indirectly from the information collection device 110. In some embodiments, the scan data may be directly obtained from the information collection device 110. After setting parameters through the user interface 160, the user may control the information collection device 110 to collect data directly through the image processing system 120. In some embodiments, the scan data may be indirectly obtained from the information collection device 110. The data collected by the information collection device 110 may be stored in the storage 140, and be retrieved from the storage 140 whenever needed.

In 375, a scan image may be generated based on the scan data. The generation of the scan image may be performed by the image processing system 120. In some embodiments, the data processing module 320 of the image processing system 120 may generate the scan image based on the scan data. In some embodiments, scan data in a non-image domain may be transformed into a scan image, and then the scan image may be displayed to the user. During a process of generating the scan image, operation 375 may also include one or more steps of data/image processing operations (e.g., data format transformation) on the scan data. The generated scan image may be sent to the image processing module 340, or output through the input/output module 310 (e.g., output to the storage 140).

In some embodiments, the information collection device 110 may be a CT device. The data corresponding to the intensity of a response signal in the obtained CT data may be transformed into grayscale data through a grayscale function (more detailed descriptions may be found in relevant descriptions of the data processing module illustrated in FIG. 3-a), and a CT scan image may be generated.

In some embodiments, the information collection device 110 may be an MRI device, and the scan data obtained by the information collection device 110 may be K-space data. The obtained K-space data may be operated according to at least one transformation algorithm (e.g., the Fourier transform algorithm) for transforming the distribution of the signal intensity in frequency space into the distribution of the signal intensity in the geometric space. Then an MRI scan image may be generated according to the grayscale function. Other types of scan data may also be transformed into corresponding scan images.

In some embodiments, the scan data may be pre-processed before the scan image is generated based on the scan data. For example, the scan data may be a series of incomplete K-space data obtained by the partial parallel acquisition technique through an MRI coil array. Therefore, before generating the scan image based on the scan data, complete K-space data may be generated based on the series of incomplete K-space data. Approaches for generating the complete K-space data based on the incomplete K-space data may be the SMASH algorithm, the SENSE algorithm, or the like. Based on the complete K-space data, the MRI scan image may be generated after operations based on, such as Fourier transform and grayscale function.

In some embodiments, the preliminarily generated scan image may be a set of two-dimensional images representing different sections of a three-dimensional object. In 375, a three-dimensional scan image may be generated based on the set of two-dimensional scan images via a three-dimensional reconstruction operation. In some embodiments, the preliminarily generated scan image may include at least one artifact or noise. In 375, the image may be outputted after being operated according to one or more steps for removing artifacts or denoising based on one or more algorithms. In some embodiments, at least one of the preliminarily generated scan images may be transformed from different types of scan data, such as CT data, MRI data, ultrasound data, X-ray data, etc. In 375, at least one fused image may be further generated based on the scan images. The fused image may then be output.

In 380, the image may be processed. The image may be processed by the image processing system 120. In some embodiments, the image may be processed by the image processing module 320 of the image processing system 120. Images to be processed may be a scan image output by the data processing module 320, or an image retrieved from the storage 140. The image processing may include medical image analysis processing operations including image segmentation, image fusion, image recognition, texture model association, image display effect adjustment, or the like, or a combination thereof.

In some embodiments, the image processing module 340 may associate an image with a texture model, or edit a texture parameter. The processed image may be generated in 390. In some embodiments, the grayscale image generated in 375 may be associated with at least one texture model. The descriptions of image processing are provided elsewhere in the present application in connection with, for example, FIG. 4-b.

In 390, an output image may be generated. The generation of the output image may be performed by the image processing system 120. In some embodiments, the image processing module 320 or the interface module 360 in the image processing system 120 may generate the output image. The output image may be sent to the storage 140 for storing, or may be sent to the user interface 160 or the human interface device 130 for display. In some embodiments, a full-color output image may be generated in 390 based on the grayscale image generated in 375.

In some embodiments, the image processing of the operation 380 and the image output of the operation 390 may be performed synchronously. For example, each time when the operation 380 is performed, an output image may be generated in 390 accordingly. The output image may be further graphically presented through the user interface 160 or the human interface device 130. The user may know the process or progress of the operation through the user interface 160 or the human interface device 130.

In the process of generating the output image, at least one parameter of a pixel/voxel may be retrieved from the image to be output. A texture model to be associated with the pixel/voxel may be obtained according to the at least one parameter. The output color of the pixel/voxel may be determined based on the texture model. The original color of the pixel/voxel may be replaced with the output color to obtain a new pixel/voxel. As used herein, the "color" (e.g., the output color, the original color) of a pixel/voxel may generally referred to as one or more parameters (or data) associated with the pixel/voxel for indicating, when the pixel/voxel is visualized via a visualization device (e.g, a display), the color of the visualized pixel/voxel. The output image may be generated based on the new pixel/voxel. The output image may be used to display the image, or enhance the display effect of an original image to be output. The output image may be displayed by the user interface 160 or the human interface device 130.

In some embodiments, the process of generating the output image may be further affected by an operation performed by the user on the user interface 160. For example, the user may perform operations of scaling, rotating, cropping, selecting and highlighting on the displayed image on the user interface 160. These operations may affect the final display effect of the image. In some embodiments, operation 390 may further include a rendering operation, so as to display at least one three-dimensional image on a two-dimensional display. In some embodiments, more detailed descriptions of generating the output image may be found in relevant descriptions of FIG. 6.

It should be noted that the above descriptions of the image processing flow of the image processing system 120 are provided for convenience of description only, and not intended to limit the present application within the scope of the illustrated embodiments. It should be understood that, for a person having ordinary skills in the art, after understanding the principles of the flow, at least one operation of the image processing flow may be changed in detail. For example, the at least one operation may include adjusting the order of operations, merging operations, splitting operations, removing at least one operation (e.g., operation 370, operation 375), adding at least one operation, or the like. These changes will not depart from the scope of the claims.

FIG. 4-a shows a schematic diagram of an image processing module according to some embodiments of the present application. The image processing module 340 may include an image selection unit 410, an image segmentation unit 420, an image recognition unit 430, a texture model association unit 440, and an output image generation unit 450. The image processing module 340 may further include other units (not shown in FIG. 3-a). The units may be directly or indirectly connected with each other. The units may be implemented by one or a set of devices (e.g., the processor 205, the processing module 265, a graphics processing unit). In some embodiments, a plurality of the units may be implemented by a same device or a same set of devices.

The image processing module 340 may process an image. The image may be obtained from the data processing module 320 or the storage 140. The image may be a two-dimensional image or a three-dimensional image. In some embodiments, the image may be a two-dimensional or three-dimensional grayscale image of a human body that contains information about one or more tissues or organs, such as vessels, bones, muscles and internal organs. The image may be, for example, a CT image, an MRI image, or the like. The image processing module 340 may localize the image. For convenience of description, an image processed by the image processing module 340 will be represented by the term "global image" hereinafter. An image obtained (e.g., through a user selection operation and/or an image segmentation operation) based on the global image will be represented by the term "local image". The local image may be a part of the global image. "Global" and "local" may be used only to indicate the inclusion relationship therebetween, and not limit the integrity or other characteristics of a specific object represented by the image. The local image may partially or wholly occupy the image region of the global image. A local image obtained based on a global image may be treated as another global image. The another global image may be further used to obtain other local images.

The image selection unit 410 may obtain a local image by selecting a local region of an image. The image may be obtained from the data processing module 320, the input/output module 310, or the image segmentation unit 420. For example, the user may perform an image segmentation operation on an image via the image segmentation unit 420 to obtain a local image, and then select the local image.

The selection operation may be an interface operation performed by the user on at least one interface element of the user interface 160. The image selection unit 410 may label the image region selected by the user as a local image, or copy all the pixels/voxels of the region to generate a local image. The image selection unit 410 may obtain a user instruction for selecting a particular region of the image from the interface module 360. The user instruction may be generated based on one or more interface operations. The image selection unit 410 may analyze the image region (for determining which pixels/voxels are included) selected by the user based on the user instruction, and obtain a new local image by labeling the image region (for labeling which pixels/voxels are included) or generating a copy of the image region based on the result of the analysis.

By way of example, the user may select an image region by box-drawing around a part of user interface 160 by using a mouse. The drawn box may represent an image region. The box-drawing operation may be implemented by pressing at least one button on the mouse and dragging the mouse at the same time. In the process of the box-drawing operation, a dynamic graph with a shape changing with the dragging of the mouse may be generated on the user interface 160, and after the box-drawing operation, an image region enclosed by the dynamic graph may be selected. The dynamic graph may be rectangular (e.g., generated by drawing a diagonal), circular (e.g., generated by drawing a radius), oval (e.g., generated by drawing a diagonal of a circumscribed rectangle thereof), polygonal (e.g., generated by drawing a series of substantially end-to-end connected straight lines), or any arbitrary shape (e.g., generated by drawing the sidelines directly by the user). The user may also perform the box-drawing operation on the touch screen through a finger. For example, the user may press the screen and drag the finger to perform the box-drawing operation. The box-drawing operation may be transformed into a user instruction for selecting an image. A range covered by the generated dynamic graphic may be transformed into coordinate range information. The image selection unit 410 may obtain at least one pixel/voxel within the coordinate range according to the user instruction and the coordinate range, and generate a local image based on the at least one pixels/voxel.

In some embodiments, the image selection unit 410 may select existing local images. The existing local images may be generated in the previous operations by the image selection unit 410 or the image segmentation unit 420. For example, after analyzing the selected image region (or a pixel), the image selection unit 410 may recognize that at least one pixel/voxel of the selected region belongs to an existing local image. The image selection unit 410 may select (e.g., based on at least one interface operation performed by the user) the existing local image, or generate a new local image.

The image segmentation unit 420 may perform the image segmentation operation on an image to obtain one or more local images. The image may be obtained from the data processing module 320, the input/output module 310, or the image selection unit 410. For example, the user may select a local image through the image selection unit 410, and then perform the image segmentation operation on the local image. Pixels/voxels that meet a condition of segmentation may be selected from a global image by the image segmentation algorithm, and a local image may be obtained based on the pixels/voxels. The target of the image segmentation may be an organ, an organism, a foreign body, a lesion, a tumor, or the like, or a combination thereof. The image may correspond to a head, a chest, an abdomen, an organ, a bone, vessel, or the like, or a combination thereof. The image segmentation may be performed based on corresponding features of pixels/voxels of the image. The corresponding features of the pixels/voxels may include texture features, such as the grayscale, the average grayscale, the hue, the saturation, the contrast, the brightness, or the like, or a combination thereof. The corresponding features of the pixels/voxels may include the spatial features, the category of the image to which it belongs, or the like.

The image segmentation unit 420 may segment the image based on one or more algorithms. The algorithms may be a threshold-based segmentation algorithm, an edge-based segmentation algorithm, a region-based segmentation algorithm, a clustering-based segmentation algorithm, or the like, or a combination The threshold-based algorithm may include obtaining one or more grayscale thresholds based on a grayscale feature of the image. The grayscale value of each pixel in the image may be obtained and compared with the one or more grayscale thresholds. The pixels may be allocated to an appropriate category based on the result of the comparison. The threshold-based segmentation algorithm may include a single threshold method, a multi-threshold method, or a global threshold method and a local threshold method. The approaches for selecting the thresholds may include an image grayscale histogram peak-valley approach, a minimum error approach, an Ostu approach, and/or a maximum entropy automatic thresholding approach, or the like.

The edge-based segmentation algorithm may include detecting an edge between regions by using the discontinuity characteristic of grayscales of pixels between different regions, so as to implement the image segmentation. The edge-based segmentation algorithm may include a serial edge detection approach, a parallel edge detection approach (e.g., using a Roberts operator, a Sobel operator, a Log operator, and/or a Canny operator), a surface fitting approach, a boundary curve fitting approach, a serial boundary searching approach, or the like.

The region-based segmentation algorithm may include two basic forms: region growing and region division merge. The former may be implemented by gradually merging single pixels to form a desired segmentation result. The latter may be implemented by gradually splitting or merging the entire image to form a desired segmentation result. The region-based segmentation algorithm may include a region growing approach, a region division-merge approach and a watershed approach.

The clustering-based segmentation algorithm may divide a set of samples (e.g., an image) into several subsets (e.g., image regions) according to the similarity between samples, and the result of the division may maximize a criterion that represents clustering quality (e.g. a distance or a similarity). The clustering-based algorithm may include a graph segmentation approach.

In some embodiments, a morphology-based segmentation approach, a statistical recognition based segmentation approach, a neural network based segmentation approach, a wavelet transform based segmentation approach, or an energy function based segmentation approach may be used.

In some embodiments, the image segmentation unit 420 may include a plurality of segmentation subunits (not shown in FIG. 4-*a*) with different segmentation objects, such as a bone segmentation subunit, a vessel segmentation subunit, a liver segmentation subunit and a lesion subunit. These segmentation subunits may include various segmentation functions. For example, the vessel segmentation subunit may include a hepatic portal vein segmentation function, a coronary artery segmentation function, an entire vessel segmentation function, a lower limb vessel segmentation function, or the like.

In some embodiments, the image segmentation unit 420 may add object category information of the object represented by the local image to the local image obtained by segmentation. The adding may be performed automatically or at least partially manually. For example, the user may trigger a vessel segmentation operation on the global image to segment a local image representing vessels. The image segmentation unit 420 may add object category information representing the vessels to the local image automatically or at least partially manually. For a local image obtained through a liver segmentation operation triggered by the user, the image segmentation unit 420 may also add object category information representing a liver to the local image.

In some embodiments, a local image may be added with at least one piece of object category information of the object. For example, a local image of hepatic portal vein may have a piece of high-level object category information indicating that the local image is an image of vessels. The local image of hepatic portal vein may also have at least one piece of low-level object category information indicating that the local image is an image of, for example, veins, liver vessels, hepatic portal veins, lesions, and/or lesion vessels. In some embodiments, the user may perform an image segmentation operation to segment a plurality of associated subordinate local images. For example, when the user performs a digestive system segmentation operation, not only a local image representing the entire digestive system may be obtained, but also a plurality of local images representing a stomach, a liver, intestines, etc., may be obtained.

The image recognition unit 430 may intelligently recognize a local image to determine the category of the object represented by the local image. For example, after a local image is obtained by one or more data segmentation algorithms, the image recognition unit 430 may analyze the local image to determine whether the local image is an image of a vessel or a bone. Moreover, the image recognition unit 430 may determine whether the image of the vessel is an image of liver vessels or kidney vessels.

The approach of the image recognition may be based on template matching. The template-matching based approach may include pre-processing an image (e.g., separating an image region from the background, enhancing the image), extracting features (e.g., a grayscale histogram feature, an anatomy feature) from the pre-processed image, selecting a template library (for example, selecting a template library for matching the image according to at least one feature extracted from the image or an operation performed by the user), image matching (for example, comparing the extracted features with features stored in the template library or features extracted from the template image). The image may be recognized based on the result of the template matching (e.g., the degree of similarity of the extracted features).

In some embodiments, the image recognition unit 430 may add the identified object category to the local image after the category of the object represented by the local image is identified. The identified object category may be added to corresponding local images automatically or at least partially manually. In some embodiments, the image recognition unit 430 may not be necessary.

The texture model association unit 440 may associate a texture model with a local image. The texture model is a model that is related to the display effect of the image. The display effect of the image may include color, perspective effect, reflection effect, or the like, or a combination thereof. The texture model may include at least one texture parameter. The texture parameter may include parameters representing one or more texture properties including color, perspective effect, reflection effect, or the like. Texture parameters may include grayscale, brightness, contrast, saturation, hue, transparency, refractive index, reflectivity, shiness, ambient light, diffuse light, specular effect, a specular scattering coefficient, etc. The texture model may generate a new display effect for the image based on the display effect of an image itself. Alternatively, the texture model may generate a texture based on the property of an image itself and applies the texture when the image is outputted (e.g., for storage or display).

Texture model may be applied to a bitmap image or a vector image. In the bitmap image, a basic application unit of the texture model may be a point. In the vector diagram, a basic application unit of the texture model may be an object. The texture model will be described by taking the bitmap as an example in the present application, but this is not intended to limit the scope of application of the texture model. In the present application, the texture model will also be described in an RGBA system, but this is not intended to limit the color system to which the texture model is applicable.

The texture model may generate a new color for a pixel/voxel based on color parameters of the pixel/voxel. The texture model may include at least one texture parameter. The at least one texture parameter may affect the newly generated color. A texture model may have a set of default texture parameter settings. At least one texture parameter of the texture model may be editable or non-editable. The texture model may include at least one function. In some embodiments, the color parameter of a pixel/voxel is a grayscale parameter (i.e., a parameter representing a grayscale), and the texture model may obtain a specific color based on the grayscale parameter and at least one texture parameter. For example, for an RGBA system, the texture model may have the form of Equation (1):

$$RGBA(r,g,b,a)=RGBA(f_R(X),f_G(X),f_B(X),f_A(X)), \quad (1)$$

wherein X refers to the grayscale of the pixel/voxel for transformation, r, g, b, and a refer to dependent variables for X in the R channel, G channel, B channel, and A channel, respectively. $f_R(X)$, $f_G(X)$, $f_B(X)$, and $f_A(X)$ refer to color scale functions for the R channel, G channel, B channel and A channel, respectively. One color scale function may return a specific color scale number based on X. A specific color may be determined by using generated color scale numbers of different channels.

In some embodiments, the function types of $f_R(X)$, $f_G(X)$, $f_B(X)$, and $f_A(X)$ may be at least partially same or completely different. Taking the color scale function $f_R(X)$ of the R channel as an example, $f_R(X)$ may be a constant function, a linear function, a quadratic function, an exponential function, a trigonometric function, or the like, or a combination thereof. The combination of different functions may form a piecewise function, a composite function, or a superposition function. In some embodiments, $f_R(X)$ may be a linear function, and $f_R(X)$ may be expressed by Equation (2):

$$f_R(X)=[A \times X + B], \quad \text{Equation(2)}$$

wherein A and B refer to constants, operator [ ] refers to a rounding operation. In Equation (2), A and B may be obtained by performing a calculation on the texture parameters in the texture model. The texture parameters for calculating A and B may relate to at least one of brightness, contrast, sharpness, hue, reflectance, or the like. The color scale functions of different channels may have different values of A and different values of B. For the color scale function $f_A(X)$ of a transparency channel, the texture parameters for calculating A and B may further include transparency, or the like. The specific values of the texture parameters may be default values in the texture model or the values edited by the user. A specific color may be generated by substituting a grayscale of a pixel/voxel into the texture model. For example, color RGBA (205, 13, 0, 142) may be outputted by applying a vessel texture model to a pixel/voxel with a grayscale of 800.

In some embodiments, parameters for calculating A and B may further include a parameter relative to an object category of the local image to which the pixel/voxel belongs. The difference of the object categories may affect specific values of A and B in a color scale function of at least one color channel. For example, a texture model is applied to a pixel/voxel with a grayscale of 800. When the pixel/voxel belongs to a vessel image, the output color may be RGBA (205, 13, 0, 142); when the pixel/voxel belongs to a bone image, the output color may be RGBA (128, 143, 132, 18); when the pixel/voxel belongs to a vein image, according to different output modes, the output color may be RGBA (205, 13, 0, 142), which corresponds to a high-level category, e.g., a vessel category, or RGBA (185, 7, 54, 142), which corresponds to a low-level category, e.g., a vain category. In some embodiments, parameters for calculating A and B may not include the parameter relative to the object category of the local image to which the pixel/voxel belongs.

In some embodiments, the imaging system 100 may include a texture model library. The texture model library may include a plurality of texture models of a same or different preferred application categories. The preferred application category may represent the category of the object represented by an image with which a texture model is suitable to be associated. For example, a texture model of which the preferred application category is the vessel category may generate a red output image based on a grayscale image. The preferred application category may represent a tissue or an organ (e.g., a bone, a vessel, a muscle, an interior organ, a nerve).

In some embodiments, a texture model may be categorized in the texture model library according to its preferred application category. For example, a texture model which is preferably applied to the vessel image may be assigned to the vessel category in the texture model library. For example, a texture model which is preferably applied to the bone image may be assigned to the bone category in the texture model library. For convenience of descriptions, the texture model of which the preferred category is the vessel category will be described by using a vessel texture model in the present application; the texture model of which the preferred type is the bone category will be described using a bone texture model in the present application, etc. It should be noted that the name of the texture model is not intended to limit the type of image it may be associated with. For example, a vessel texture model may be associated with either a vessel image or a bone image (e.g., based on the user's interface operation).

In some embodiments, the category of the texture model may include at least one sub-category. For example, the vessel category may include an artery sub-category, a vein sub-category, a capillary sub-category, or the like. The subcategories may be further refined. A texture model may be assigned to at least one category. For example, for a texture model which is preferably applied to a coronary artery, it may be assigned to at least one of a vessel category, an artery category and a heart category.

The texture model may be obtained in various ways, such as program installation, downloading from the Internet or a database, user-customized generation, etc. In some embodiments, the texture model may be added to the storage 140 through an installation program. The program implementing the function of the image processing module 340 may be at least one image processing program. The installation program may be an installation program of the image processing program or a function expansion upgrade package of the image processing program. In some embodiments, the texture model may be added to the storage 140 through the human interface device 130 or the network 150. For example, the texture model may be inputted into the storage 140 in a manner of compiling code encoded by the user. The texture model may be obtained from the network 150 by the user or the imagining system 100.

The texture model may be generated using various approaches. The generation approach may be large data calculation, user customization, machine learning, induction, prediction, data fitting, or the like. The generation process of the texture model may be illustrated as the process of determining a texture model parameter, and the generation approach of the texture model may be the approach to determine the texture model parameters.

In some embodiments, the texture model may be generated with an approach of large data calculation. The generation approach may include determining at least one scan image, extracting a texture parameter based on the at least one scan image, and establishing a texture model based on the extracted texture parameter. The scan image may be at least one scan image based on usage habits of the user. The scan image may be at least one scan image selected by the computer from a scan image database according to certain rules.

In some embodiments, the texture model may be generated by a user-customizing approach. For example, the user may generate a new texture model by editing parameters of a texture model generation template (the template may be provided by the image processing program). In some embodiments, the user may edit at least one texture parameter based on an existing texture model to generate a new texture model. In some embodiments, the texture model may be stored in a saved file of an output image generated based on operation 390. The user may acquire a texture model satisfying the costumed condition from the saved file based on the display effect of the output image. In some embodiments, the user may import at least one texture model from other image processing programs.

In some embodiments, the texture model may be generated by an approach of machine learning. The approach of machine learning may be in the form of supervised learning, unsupervised learning, semi-supervised learning or enhanced learning. For example, in the process of generating a texture model according to the supervised learning, a function may be learned from one or more given scan images. The function may be a possible texture model corresponding to the one or more scan image. The machine learning algorithm may include an artificial neural network, a decision tree, Gaussian process regression, a linear discriminant analysis, a nearest neighbor method, a radial basis function kernel, a support vector machine, etc.

In some embodiments, the texture model may be generated by an approach of data fitting. The user may obtain a full-color image and a grayscale image for generating the full-color image. The user may retrieve at least one pixel/voxel of the full-color image and extract its color parameter. The user may retrieve at least one pixel/voxel corresponding to the at least one pixel/voxel image of the full-color image in the grayscale image and extract its grayscale parameter. The user may obtain the texture model by fitting the at least one color parameter and its corresponding grayscale parameter. The fitting approach may be linear fitting, curve fitting, segmentation fitting, or the like. The algorithms for implementing fitting may be least squares, the Gaussian algorithm, the Ransac algorithm, the Levenberg-marquardt algorithm, the trust-region-reflective algorithm, etc.

The associated operation between the texture model and the image performed by the texture model association unit 440 may be implemented by adding a recognition parameter representing the texture model to the image. The recognition parameter may be used to obtain the texture model. For example, the recognition parameter may be a storage address of the texture model, or a parameter pointing to the storage address, etc. The adding the recognition parameter to the image may be performed in images. For example, the recognition parameter may be added to the data representing overall properties of the image. The adding the recognition parameter to the image may be performed in at least one pixel/voxel in the image. For example, the recognition parameter may be added to each pixel/voxel in the image.

After a texture model is associated with an image, when the image is outputted (generating an image file or displaying by the human interface device 130), the color of each pixel/voxel may be a color generated by the texture model associated with the image for the pixel/voxel. The texture model may be an independent model stored in the storage 140. When the texture parameter of the texture model is edited, the display effect of at least one image associated with the texture model may be changed correspondingly. For example, after changing the main color of a texture model from red to blue by editing the texture parameter of the texture model, the main color of at least one image associated with the texture model may be changed from red to blue correspondingly. In some embodiments, by editing the texture parameter, operations such as a highlight display, a boundary and contour enhancement display may be performed on at least one image associated with the texture model.

In some embodiments, the texture model may correspond to an interface element on the user interface 160. Different texture models may be associated by selecting different interface elements. The user may associate at least one local image with at least one texture model. Different local images may be associated with a same texture model. In some embodiments, the imaging system 100 and/or the user may match each object category with a same or different texture models. When a local image is associated with a plurality of different texture models, the different texture models may have different output levels. The output level represents the priority of the texture model called when the image is output.

The output image generation unit 450 may generate an output image based on the image processed by the image processing unit 340. The output image generation unit 450 may further output the output image through the input/output module 310. The image may be displayed on the user interface 160 or the human interface device 130, or be stored in the storage 140. In outputting the image, the color or the display manner of the output image may be determined by the texture model. The output image may be a full-color image or a grayscale image that has a color different from the scan image.

The output image generation unit 450 may retrieve at least one parameter of a pixel/voxel from the scan image. The texture model associated with the pixel/voxel may be obtained through the at least one parameter. The at least one parameter may include a coordinate parameter representing the spatial position of the pixel/voxel, a color parameter representing the original color of the pixel/voxel, a classification parameter representing the local image to which the pixel/voxel belongs, an association parameter representing the texture model associated with the local image to which the pixel/voxel belongs, etc. The coordinate parameter and the color parameter maybe necessary, and other parameters may be optional. In some embodiments, the color parameter may be a grayscale parameter. The output color of the pixel/voxel may be determined based on the texture model.

The output image generation unit 450 may generate a new color parameter based on the output color determined by the texture model. The output image generation unit 450 may generate a new pixel/voxel by using the new color parameter and other parameters (e.g., the coordinate parameter) other than the at least one color parameter of the retrieved pixel/voxel. The output image may be output based on the new pixel/voxel.

The output image generation unit 450 may further adjust the output image. For example, the output image generation unit 450 may change the display of the output image on the user interface 160 based on the operations of scaling, rotating, cropping, selecting and highlighting. The operations may be performed by the user on the image displayed on the user interface 160. The output image generation unit 450 may have an image rendering function. The output image generation unit 450 may render a three-dimensional output image to display the three-dimensional output image on a two-dimensional display.

It should be noted that the above descriptions of the image processing module 340 and its various units are provided for convenience of description only, and not intended to limit the present application within the scope of the illustrated embodiments. It should be understood that, for a person having ordinary skills in the art, after understanding the principles of the system, the various components in the image processing module 340 may be arbitrarily combined, split, or changed in detail. At least one unit, such as the image recognition unit 430, may be removed from the image processing module 340.

FIG. 4-b is a flowchart illustrating an exemplary process of image processing performed by the image processing module 340 according to some embodiments of the present application. Process 400 may be an exemplary description of a possible embodiment of 380 in FIG. 3-*b*. One or more operations of the process 400 may be performed by the devices illustrated in FIG. 2-*a* and/or FIG. 2-*b*.

In 460, a local image may be obtained based on a global image. The obtaining of the local image may be performed by the image selection unit 410 and the image segmentation unit 420, individually or jointly.

In some embodiments, the image selection unit 410 may obtain a local image based on at least one user instruction. For example, the user may perform an interface operation on at least one interface element of the user interface 160. The interface operation may be transformed into a user command representing the selection of an image (for example, the interface operation may be transformed through the interface module 360). The user instruction may include a selection range parameter of an image. The image selection unit 410 may analyze the image region (e.g., which pixels/voxels may be included in the image region) selected by the user according to the image selection range parameter and obtain a local image based on the analysis result.

In some embodiments, the image segmentation unit 420 may select a portion or all of the pixels/voxels satisfying a segmentation condition in a global image. The image segmentation unit 420 may obtain a local image based on the pixels/voxels (for example, an image may be obtained through at least one image segmentation algorithm). The image segmentation unit 420 may add object category information to the local images automatically or at least partially manually. For example, the image segmentation unit 420 may perform a bone segmentation operation on the global image to segment a local image representing bones, and automatically add an object category parameter of the bones to the local image.

In some embodiments, in 460, another local image may be obtained based on a local image obtained from the global image. In some embodiments, in 460, an image segmentation operation or a user selection operation may be firstly performed on the global image to obtain a local image, and then another image segmentation operation or a user selection operation may be performed on the local image to obtain another local image. For example, in 460, a liver segmentation operation may be firstly performed on the global image to obtain a liver image, and then a vessel segmentation operation may be performed on the liver image to obtain a liver vessel image. In 460, the local image of the region where the liver is located may be firstly obtained from the global image through a selection operation by a user based on anatomical experience. The vessel segmentation operation may be performed on the local image to obtain a liver vessel image, and then a user selection operation or a lesion recognition/segmentation operation may be performed on the liver vessel to select the lesion vessels.

In some embodiments, in 460, after the user selection operation and the image segmentation operation are performed, the image processing module 340 may automatically analyze and identify (e.g., through the image recognition unit 430) the categories of one or more objects included in the region, and automatically segment images representing the one or more objects. For example, after the user select a region with a liver through the user selection operation, since the user's operation may be inaccurate, the selected image region may contain an image representing one or more different objects. The image processing module 340 may automatically identify the category of the object represented by the image contained in the region, and determine one or more object categories which are most likely to be selected by the user. Because the image representing the liver has a higher proportion in the region, the image processing module 340 may determine that the user may have a great chance of selecting the liver, and automatically call the image segmentation unit 420 to segment the liver and obtain an accurate liver image. Alternatively, in 460, after cerebral vessels are segmented through the image segmentation operation, the image processing module 340 may recognize a hemangioma in the process of segmentation. The image processing module 340 may simultaneously output two segmented images representing cerebral vessels and hemangiomas, respectively, and add different object category information to and/or associate different texture models with the two segmented images.

In 470, a category of an object represented by the local image may be identified. The identification may be performed by the image recognition unit 430 at least partially manually or automatically. Alternatively, the local image may be identified by the user based on experience. The recognition approach may be an approach based on the template matching. For example, the category of the object represented by the image may be identified through approaches of modeling by extracting the shape of the local image, the grayscale distribution feature, or the like (e.g. a grayscale histogram), and matching the local image with a standard image (e.g., an image stored in the storage 140). The approximate range of the object category represented by the image may be determined in a manner such as performing anatomical analysis on the specific spatial position where the local image located in the global image. For example, a bone image may be determined to be a sacrum image by intelligently or manually recognizing the bone image. The identified object category may be added to a corresponding local image by the image recognition unit 430 automatically or at least partially manually, or be directly added to a corresponding local image through a user instruction. In some embodiments, the object category information of the local image may be directly determined by the image segmentation unit 420, and thus the image recognition unit 430 and 470 may be optional. In some embodiments, the operation 470 and the operation 460 may be performed synchronously. For example, an object category of the image or an object category of at least one sub-image of the image may be intelligently identified while an image is segmented. In some embodiments, the operation in 480 does not need object category information of the sub-image, and 470 may be skipped.

In 480, the local image may be associated with a texture model. The association operation may be performed by the texture model association unit 440. The texture model may be obtained from the storage 140 through the input/output module 310. The operation of associating the texture model with the local image may be implemented by adding a recognition parameter representing the texture model to the image. In some embodiments, the image associated with the texture model may be a grayscale image. The texture model may generate a corresponding color based on the grayscale information of each pixel/voxel in the image, thereby generating a color output image based on the grayscale image in 390. In some embodiments, the texture model may further change the generated color according to the information of object represented by the image. In some embodiments, the object category of the image may affect the category of texture model to be associated with. The user may determine which one or which category of texture model is used to associate the image with at will.

In some embodiments, the association operation of the texture model may be automatically performed through the image processing module 340. For example, in 460 or 470, after the object category of an image is determined, the image processing module 340 may automatically match or associate the image with a texture model from the corresponding texture model library. In some embodiments, a texture model parameter may be set for at least one image segmentation algorithm. The texture model parameter may represent a texture model or a parameter to identify it. When a local image is obtained through the image segmentation algorithm, the local image may be automatically associated with the texture model corresponding to the texture model parameter. In some embodiment, the process of adding an object category to the image may be optional. More descriptions of the texture model association operation may be found in FIG. 5 and the related descriptions thereof.

It should be noted that the above descriptions of the process of image processing by the image processing module 340 are provided for convenience of description only, and not intended to limit the present application within the scope of the illustrated embodiments. It should be understood that, for a person having ordinary skills in the art, after understanding the principles of the process, one or more operations of the process of image processing may be changed, including, for example, adjusting the order of operations, merging operations, splitting operations, removing at least one operation (e.g., operation 470), adding at least one operation, etc. These changes do not depart from the scope of the claims.

Figure 5:
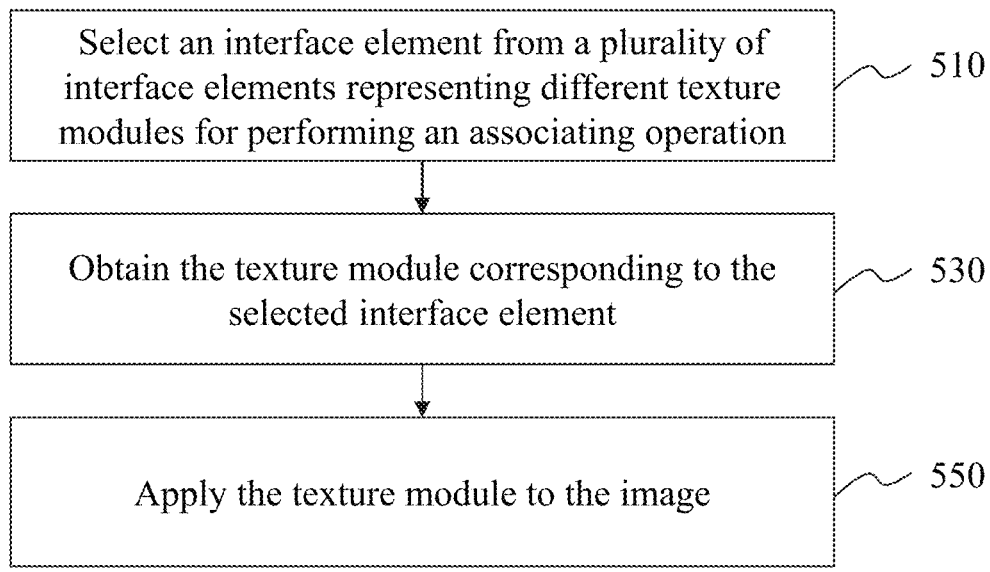
FIG. 5 is a flowchart illustrating an exemplary process of associating an image with a texture model according to some embodiments of the present application.

FIG. 5 is a flow chart illustrating an exemplary process of associating an image with a texture model according to some embodiments of the present application. Process 500 may be an exemplary description of a possible embodiment of 380 in FIG. 3-*b*. Operations of the process 500 may be performed by the devices illustrated in FIG. 2-*a* and/or FIG. 2-*b*.

In 510, an interface element may be selected from a plurality of interface elements representing different texture models for performing an association operation. The user interface 160 may provide a series of interface elements representing different texture models. The user interface 160 may display at least one interface element corresponding to a certain texture model. The texture model may be displayed in the form of a texture ball on the user interface 160. Detailed descriptions of the texture ball and the interface element may be found in FIG. 7-*b* and the related descriptions thereof. A texture ball may be selected from a series of texture balls provided by the user interface 160. The association operation may be performed by the texture model association unit 440.

In some embodiments, the operation of selecting and determining the texture ball may be the associated operation. The selection may be performed according to the appearance effect of the texture ball or the corresponding pattern/text descriptions. In some embodiments, the user may perform the selection operation and the associated operation on the texture ball through the human interface device 130. Optionally, after the association operation is completed, the human interface device 130 may pop up an operation confirmation dialog box or use a voice prompt to ask the user to confirm the association operation. The user may perform the association operation in one or more ways. For example, the user may select a texture ball through hovering or clicking on the texture ball, and then perform the association operation on the texture ball in a manner such as dragging or double-clicking. For another example, the user may click on the texture ball to select a texture ball through a touch screen operation, and then perform the association operation on the texture ball in a manner such as dragging or long pressing. As another example, the user may select and associate a texture ball by using a voice command in a voice control manner. As a further example, the user may select and associate a texture ball through a gesture.

In 530, the texture model corresponding to the selected interface element may be obtained. The operation to obtain the texture model may be performed by the texture model association unit 440. The user's selection or associated operation of the texture ball may be transformed into a user instruction. The associated operation may be performed through the interface module 360. Through the user instruction, the texture model association unit 440 may call the input/output module 310 to obtain, from the storage 140, the network 150, or the human interface device 130, information corresponding to the associated texture model. The information corresponding to the associated texture model may include the information of the name (or the classification number) and the storage address of the texture model.

In 550, the texture model may be applied to the image. In some embodiments, a recognition parameter may be generated based on the information of the texture model obtained in 530. The recognition parameter may be added to the local image. The recognition parameter may be added to the parameters of the overall properties of the local image or to the parameters of each image element (e.g., a pixel/voxel). The addition of a parameter may be performed in various manners. The addition of a parameter may refer to changing a parameter in a data unit from one value (e.g., a NULL value) to another value (e.g., a value representing a recognition parameter). The addition of a parameter may also be achieved by the following operations: firstly, defining a new data format (e.g., a new image data format). The new data format may include some or all parameter types of an existing data format (e.g., an existing image data format) and one or more new parameter types corresponding to the parameters to be added. secondly, generating a new data unit (e.g., an image element of an image using the new data format) using the new data format; then, inputting a portion of or the whole data of an existing data unit (e.g., an image element of an image using the existing data format) into the new data unit, and inputting the parameter to be added into the new data unit (e.g., the recognition parameter). After the association of the texture model is completed, each pixel/voxel of the associated image may retain information of its original color, and the color for display may be generated through the texture model associated with the associated image. The user may store the associated image and generate a new image file which may include relevant data of the texture model used.

It should be noted that the above descriptions of the texture model are provided for convenience of description only, and not intended to limit the present application within the scope of the illustrated embodiments. It should be understood that, for a person having ordinary skills in the art, after understanding the principles of the process, at least one operation of the flow may be changed in detail, including, for example, adjusting the order of operations, merging operations, splitting operations, removing at least one operation, adding at least one operation, etc. These changes do not depart from the scope of the claims.

Figure 6:
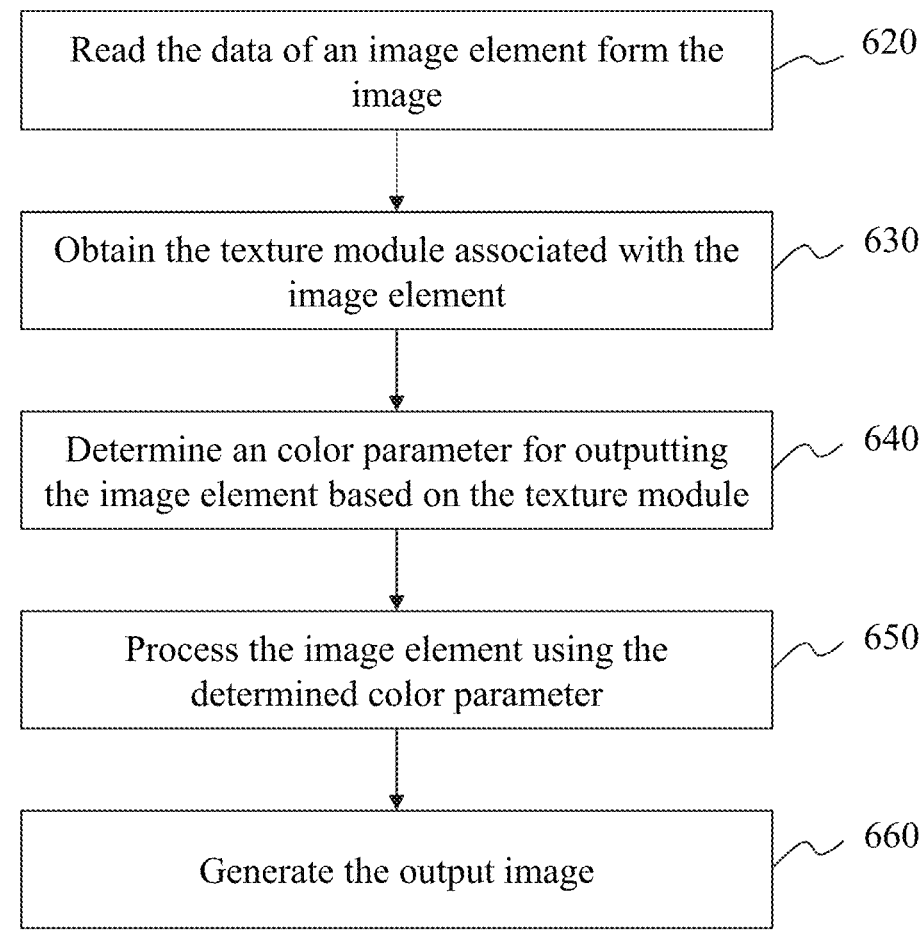
FIG. 6 is a flowchart illustrating an exemplary process of generating an output image according to some embodiments of the present application.

FIG. 6 is a flowchart illustrating an exemplary process of a method for generating an output image according to some embodiments of the present application. Process 600 for generating the output image may be performed by the image processing system 120 illustrated in FIG. 3-*a*. In some embodiments, the process 600 may be an exemplary description of a possible embodiment of 390 in FIG. 3-*b*. The generated output image may be displayed on a display device (e.g., the user interface 160, the human interface device 130), or stored in a storage device (e.g., the storage 140). Operations of the process 600 may be performed by the devices illustrated in FIG. 2-*a* and/or FIG. 2-*b*.

In the process of generating the output image, the process 600 may process the image with the image element as a basic unit. The image element may be a pixel/voxel or a group of pixel elements (e.g., a plurality of pixels/voxels of the image). The processing sequence of the image elements may be random or according to certain rules. For example, the process 600 may process the image elements according to a certain spatial coordinate sequence. When a global image including at least one local image is processed, the image elements of the at least one local image may be processed. The processing of other image elements may be continued stopped. The process of generating the output image in FIG. 6 may be applied to generate an output image of a non-partitioned image or an output image of a global image including at least one local image. For convenience of descriptions, the detailed process of generating the output image will be introduced below by taking a global image as an example. In 620, data of an image element from the image may be retrieved. The image may be a local image or a global image. Data of the image element may include data of at least one parameter of the image element. The parameter may include a position coordinate parameter of the image element, an original color parameter of the image element, a classification parameter of the local image to which the image element belongs, an association parameter representing the associated texture model of the local image to which the image element belongs, etc.

In some embodiments, the process 600 may retrieve data of each pixel/voxel in the image. The data may include the position coordinate of the pixel/voxel, the grayscale value of the pixel/voxel, and an association parameter representing the texture model associated with the local image to which the pixel/voxel belongs, etc.

In 630, a texture model associated with the image element may be obtained. The obtaining of the texture model may be performed by the texture model association unit 440. The texture model to be obtained may be determined through the classification parameter, the classification parameter, or may be determined by the imaging system 100. More detailed descriptions of the texture model may be found in FIG. 4-*b* and the relevant descriptions thereof.

In some embodiments, the image element retrieved in 620 may include an association parameter. The recognition parameter of the target texture model may be obtained through the association parameter. The association parameter may be the recognition parameter of the target texture model or a parameter pointing to the recognition parameter.

In some embodiments, the image element retrieved in 620 does not include the associated parameter but may include the classification parameter. The local image belonging to the image element may include a texture model parameter (e.g., a recognition parameter of the target texture model or a parameter pointing to the recognition parameter). The related information of the local image to which the image element belongs may be obtained through the classification parameter. Then the texture model parameter may be obtained. The recognition parameter of the target texture model may be obtained through the texture model parameter.

In some embodiments, the image element retrieved in the operation 620 may neither include the classification parameter nor the association parameter. The coordinate parameter of the retrieved image element may be analyzed and identified, and the recognition parameter of the target texture model may be obtained according to the analysis and identification result. After the recognition parameter is obtained through one or more approaches, the target texture model may be obtained based on the recognition parameter.

In 640, a color parameter for outputting the image element may be determined based on the texture model. The color parameter may be obtained from the texture model.

In 650, the image element may be processed using the determined color parameter. The image element may be processed by replacing the original color of the image element with the determined color parameter for output, so as to obtain an updated image element. The updated image element may be used to display or generate a new output image. The color of the updated image element may be determined based on the color parameter obtained from the texture model, and other parameters of the updated image element may be the same as or partially the same as the original image element. For example, the coordinate parameter of the updated image element may be exactly the same as the original image element. In some embodiments, the image processing system 120 may automatically assign a texture model to an image element that is not associated with any texture model in 630 and determine the color for outputting the image element in 640. The user may edit at least one texture parameter of the texture model.

In 660, an output image may be generated. The output image may be an image for display or an exported image. By performing operations 620 to 650 on each image element of the original image (the image for output), a set of corresponding new image elements may be generated. The new image elements may be used to construct the output image. Generating the output image does not necessarily indicate generating a new image file. When being used to display the original image or enhancing the display effect of the original image, the output image (or the displaying image) may represent a data stream for displaying the image on the user interface 160 or the human interface device 130. When the user edits at least one parameter of the texture model, the color generated in the operation 640 may be changed accordingly. During the process of displaying (outputting) an image, the texture model may be called for color determination when each image element is displayed, and the output image needs to be constantly refreshed (or generated with the refresh rate determined by the imaging system 100) even in the case when the user does not adjust the original image, such that the displaying color of at least one local image associated with the edited texture model may be changed accordingly.

In the process of generating the image, the process of generating the displaying image may be further affected by the operation of the user performed on the user interface 160. For example, the user may perform operations of scaling, rotating, cropping, selecting and highlighting on the displaying image on the user interface 160. The operations performed by the user may affect the generation of the displaying image. These effects may be reflected in any operation of operations 620 to 660, or any operations not specifically described in the present application. In some embodiments, the process of generating the output image may further include a rendering operation, so as to display at least one three-dimensional image on a two-dimensional display.

It should be noted that the above descriptions of the process of generating the output image are provided for convenience of description only, and not intended to limit the present application within the scope of the illustrated embodiments. It should be understood that, for a person having ordinary skills in the art, after understanding the principles of the process, at least one operation of the process may be changed in detail, including, for example, adjusting the order of operations, merging operations, splitting operations, removing at least one operation, adding at least one operation, etc. These changes do not depart from the scope of the claims.

FIG. 7-a illustrates a schematic diagram of a user interface according to some embodiments of the present application. The user interface 700 may be an embodiment of the user interface 160. The user interface 700 may include at least one interface element, such as an image section 701, a functional section 704 (e.g., functional section 704-1 and functional section 704-2), a secondary interface 710 and a pointer 720, or the like. The interface element may be of any number or be located at any location on the user interface 700. The interface element may be visually overlapped, interconnected or separated from each other. When a code or a program is performed to generate the user interface 700, the user interface 700 may be displayed on at least one visualization device of the interface 130. When a plurality of visualization devices are used to display the user interface 700, any one of the at least one interface element of the user interface 700 may be displayed on any one of the plurality of visualization devices. For example, a first visualization device and a second visualization device may each display an image section 701, and two functional regions 704 may be additionally displayed on the first visualization device.

The image section 701 may be an interface element for displaying an image 730. The image 730 may be a two-dimensional or a three-dimensional image. In some embodiments, the image 730 may be a two-dimensional or a three-dimensional image representing the internal structure of a human body. The image 730 may be a grayscale image. The image 730 may be a global image including at least one local image. The at least one local image of the image 730 may be associated with at least one texture model. The image section 701 may also include at least one interface element for operation assistance, for example, a grid line, a scale, or the like (not shown in FIG. 7-a). The image section 701 may display the image 730 for providing a view for the user. The user may change the display effect of the image 730 through one or more operations (e.g., zooming, moving, rotating, changing viewpoints or viewing angles). The user may select a portion or the whole image region of the image 730 in the image section 701 through one or more operations (e.g., moving a mouse, selecting rectangular box). The operation of the user in the image section 701 may open at least one secondary interface.

The functional section 704 (e.g., the functional section 704-1 and the functional section 704-2) may be an interface including at least one functional interface element. A functional interface element may correspond to one or more functions of the image processing system 120. The functional interface element may include a text or a pattern describing its function. The functional interface element may be at least one of a text box 714, a button 712, a slider 715, a selection box 716, or the like. The text box 714 may be used to display or input at least one parameter (e.g., one image segmentation parameter, one texture parameter). The button 712 may be used to confirm the execution of user operations (e.g., image selection) or functions (e.g., image segmentation, image recognition and texture model association). For example, the user may click on the button 712 through the human interface device 130 to confirm the execution of the image segmentation operation, or the like. The slider 712 may be applied to the adjustment of one or more parameter values. For example, the user may visually change the grayscale parameter value of the image through dragging the slider 715. The selection box 716 may be used to control the execution of the operation predetermined by the system. For example, the user may select whether to execute an operation of adding a reflection effect to a texture model through clicking on the selection box 716. The functional section 704 may include other types of functional interface elements. The user's operation on the functional interface elements may be transformed into user instructions.

The functional section 704 may further include a display interface element for displaying characters or images (not shown in FIG. 7-a). The display manner of the display interface element may be dynamic or static. For example, the display manner of the display interface element may be an image thumbnail, an image effect preview, a system working status display region, or the like. The display interface element may be used to provide the user with the description information of at least one interface element. The display interface element may also provide the user with dynamic prompt information on the operation being executed by the image processing system 120, working state information or self-checking information of at least one device/component of the imaging system 100, assistant information for the user's current operation (e.g., current position coordinates of the pointer 720, a local enlarged image of the image 730). An interface element may be both a functional interface element and a display interface element.

The functional section 704 may be located at the top (e.g., as a menu bar), the right side (e.g., as a side bar), the left side (e.g., as a navigation bar), the bottom side (e.g., as a task bar). The user may open at least one secondary interface 710 in the functional section 704. The manner for opening the secondary interface 710 may include operating on the functional section 704, or operating on at least one interface element of the functional section 704.

The secondary interface 710 may be displayed on the human interface device 130 after an operation is performed on the user interface 700. The secondary interface 710 may be an image section 701, a functional section 704, or the like, or a combination thereof. The part(s) of the user interface 700 other than the secondary interface 710 may be referred to as a main interface. For example, the image section 701 and the functional section 704 may be a main interface or a secondary interface. The secondary interface 710 may be displayed after an operation is performed on at least one interface element of the main interface or of another secondary interface. The secondary interface 710 may be displayed on the main interface in an overlapped manner or displayed outside the main interface. The secondary interface 710 and the main interface may be displayed through a same or different visualization devices of the human interface device 130. A user interface 700 may simultaneously display at least one main interface or at least one secondary interface 710.

The pointer 720 may assist the user's operation on the user interface 700 through the human interface device 130.

In some embodiments, the user may be assisted in selecting an interface element with the pointer 720. For example, the user may operate on the human interface device 130 (e.g., moving a mouse) to move the pointer 720 to an interface element for selecting the interface element, or to move the pointer 720 passing through a range for selecting at least one interface element. The user or the image processing system 120 may perform one or more operations based on the selected interface elements. The pointer 720 may have an arbitrary shape or size. For example, the pointer 720 may be cross-shaped, I-shaped, round, polygonal, arrow-shaped, or the like. The shape and size of the pointer 720 may be changed according to the situation. For example, the pointer 720 may have different shapes when being hovered on different interface elements, or when the image processing system 120 is performing different functions. The pointer 720 is an optional interface element. For example, the user may operate the human interface device 130 by, for example, motion, gesture, or acoustic control without the pointer 720. When the user operates the human interface device 130 by means of finger touch, the pointer 720 may be replaced by the finger.

FIG. 7-b illustrates a schematic diagram of a texture ball interface and a texture ball according to some embodiments of the present application. The texture ball 750 is an interface element on the user interface 700. One or more texture balls 750 may coexist on a texture ball interface 760. The user interface 700 may include at least one texture ball 750 or texture ball interface 760. The possible presentation forms of the texture ball 750 and the texture ball interface 760 on the user interface 700 may be found in related descriptions of FIGS. 8-a to 8-e. It should be noted that the texture ball 750 and the texture ball interface 760 may have other kinds of presentation forms, and FIGS. 8-a to 8-e are only provided for illustration purposes and not intended to limit the presentation forms may have. In some embodiments, the texture ball 750 may be displayed on the computing device illustrated in FIG. 2.

The texture ball 750 may be a visual presentation of the texture model on the user interface 700. The texture ball 750 may correspond to at least one texture model. When a texture ball corresponds to a plurality of texture models, some of the texture parameters of the plurality of texture models may be the same. For example, the texture ball 750 may correspond to a plurality of texture models of different transparencies. The visual presentation effect of the plurality of texture models may be blue. At least one texture model corresponding to at least one texture ball 750 may constitute at least one texture model database. The at least one texture model database may be stored in the storage 140 or a storage unit (not shown in FIG. 1) of the image processing system 120.

The texture ball 750 may have a same or similar display effect as that of the corresponding texture model. For example, a texture model which is preferably applied to vessels may output the grayscale image representing the vessels with a color of RGBA (184, 12, 33, 111). The corresponding texture ball 750 may also have a same or similar color with a color of RGBA (184, 12, 33, 111). The user may predict the effect of applying the corresponding texture model to the local image by observing the texture ball 750. The texture ball 750 may further include text or graphical descriptions of the preferred application range of the corresponding texture model. For example, the texture ball 750 corresponding to a texture model which is preferably applied to vessels may further include pattern and/or text descriptions representing the vessels. For convenience of descriptions, a texture ball 750 corresponding to a vessel texture model may be referred to as a vessel texture ball 750. A texture ball 750 corresponding to a bone texture model may be referred to as a bone texture ball 750.

In some embodiments, the display effect of the texture ball 750 may be generated according to the corresponding texture model in real time. If at least one texture parameter of the texture model is edited, the display effect of a corresponding texture ball 750 may also be changed accordingly, so as to facilitate the user to evaluate the effect of editing. In some embodiments, the effect of the texture ball 750 may be preset, and the texture parameter of the corresponding texture model is not editable. In some embodiments, the texture ball 750 may be directly displayed on the main interface of the user interface 700. In some embodiments, the texture ball 750 may be displayed on a secondary interface of the user interface 700, and the secondary interface may be displayed in front of the user by performing an operation on at least one interface element of the user interface 700 by, for example, opening a menu item through the mouse or long pressing an image region through the touch screen, or the like.

In some embodiments, the user interface 700 may selectively provide at least one texture ball 750 according to the object category information of the local image to be associated with. For example, a texture model library may include texture models BL1, BL2, BL3, BO1, BO2, LI1, or the like, among which BL1, BL2 and BL3 are vessel texture models, BO1 and BO2 are bone texture models, and LI1 is a liver texture model. If the local image to be associated with a texture model is a vessel image, the user interface 700 may preferentially display texture balls 750 representing BL1, BL2 and BL3 for facilitating the user's selection. In some embodiments, the user interface 160 may display the texture balls 750 representing all texture models, and the user may select a texture model such as BO1 or LI1 at will and associate it with the local image.

In some embodiments, a texture ball 750 may represent a texture theme. For example, a texture ball 750 may include texture models corresponding to images of a plurality of tissues and organs (e.g., vessels, bones, internal organs, nerves, muscles) of a human body. The texture model association operations of a plurality of local images of a global image may be achieved in one step by associating the texture ball 750 with the entire global image. By editing different texture models in the themed texture ball, at least one local image associated with the texture model in the global image may be changed.

By associating an image region (e.g., a local image) in the image 730 with a texture ball 750, the corresponding texture model may be applied to the image region. The descriptions of the association operation may be found in related descriptions of FIGS. 4-a, 4-b, 5, 9-a to 9-d, 10-a and 10-b. The term "texture ball" and the shape of the texture ball 750 in FIG. 7-b is not intended to limit the shape and/or the display effect of the texture ball 750. The texture ball 750 may be of any shape. For example, the texture ball 750 may be circular, fan-shaped, polygonal, irregularly shaped, or the like. The texture ball 750 may have the same or similar display effect as the corresponding texture model. If at least one texture parameter of the texture model is edited, the display effect of the corresponding texture ball 750 may also be changed accordingly. The texture ball 750 may be a functional interface element as well as a display interface element. In some embodiments, the texture ball 750 may be further displayed as a prediction diagram illustrating the effect of applying the corresponding texture model to an image. The image may be a part of the image 730 or an illustrative in-built image of the system. The illustrative in-built image may show a part of the region of the image after the texture model is applied.

The texture ball interface 760 may include at least one texture ball 750 or other types of interface elements (e.g., the button 712), or the like. The texture ball interface 760 may have an arbitrary size and shape (e.g., circular, fan-shaped, polygonal and irregularly shaped). A plurality of texture balls 750 of the texture ball interface 760 may be overlapped, separated, or partially overlapped with each other. The user may select a texture ball 750 from the texture ball interface 760 to associate an image with it. The user may perform an operation on at least one interface element of the texture ball interface 760 to display additional texture balls 750. For example, the texture ball interface 760 may include at least one category button (not shown in FIG. 7-b) corresponding to a set of texture balls of a particular category (e.g., a texture ball of a vessel category, a texture ball of a bone category or a texture ball of a muscle category). In some embodiments, the user may click on the category button representing the vessel category to display at least one texture ball of the vessel category, or click on the grouping button representing the bone category to display at least one texture ball of the bone category.

The texture ball interface 760 may display at least one corresponding texture ball 750 based on the type of the image to be associated with. For example, if the image needs to be associated with is the vessel image, the texture ball interface 760 may preferentially display at least one texture ball 750 of the vessel category (e.g., a texture ball of veins or a texture ball of arteries). For example, if the image needs to be associated with is the muscle image, the texture ball interface 760 may preferentially display at least one texture ball 750 of the muscle category.

The texture ball interface 760 may preferentially display the texture ball 750 of user preference. The user preference may be set by the user, retrieved from the storage 140 or calculated by the image processing system 120. The user preference may be the current image viewer's user preference, or other people's user preference. For example, an intern may adopt an attending surgeon's preferences. In some embodiments, preference information of the user who uses the texture ball 750 may be inputted through the human interface device 130. For example, a user A prefers to use the texture ball 750 of which the visual presentation effect to display the vessel image is blue. In some embodiments, the user preference information for the texture ball 750 may be retrieved from the storage 140 and the corresponding texture balls 750 may be displayed on the texture ball interface 760. The preference information may be obtained from a medical imaging device provider, a system for recording the usage of a hospital medical imaging device, a cloud database, or the like. In some embodiments, the image processing system 120 may adaptively calculate the user's preference, and preferentially select some texture balls 750 to be displayed on the texture ball interface 760 based on the calculation result.

FIGS. 8-a to 8-e illustrate schematic diagrams of the representations of the texture ball interface on the interface according to some embodiments of the present application. User interfaces 801, 802, 803, 804, and 805 may each be a specific embodiment of the user interface 700. Texture ball interfaces 811, 812, 813, 814 and 815 may each be a specific embodiment of the interface 760. Functional section 821 and functional section 822 may each be a specific embodiment of the functional section 704, respectively. Button 831 and button 832 may each be a specific embodiment of the button 712.

The functional section 821 and the functional section 822 may be main interfaces or secondary interfaces. The texture ball interface 811 may locate on the functional section 821, and the functional section 821 may locate at the right side of the user interface 801 (e.g., as a right sidebar). The texture ball interface 812 may locate on the functional section 822. The functional section 822 may locate at the top of the user interface 802 (e.g., as a top menu bar). The functional section 821/functional section 822 may also locate at the top or the left side of an interface.

The texture ball interfaces 813 and 814 may be secondary interfaces. The texture ball interface 813 may be displayed on the user interface 803 by operating (e.g., clicking on) a button 831. The button 831 may be located at a functional section of the user interface 803. The texture ball interface 814 may be displayed on the user interface 804 by operating (e.g., clicking on) a button 832. The button 831 may be located at a secondary interface 833 of the user interface 804. The texture ball interface 813 or 814 may be displayed at any position on the user interface 803 or 804.

The main interface 841 may be a main interface or a combination of a plurality of adjacent main interfaces of the user interface 805. The texture ball interface 815 may be a main interface or a secondary interface. The texture ball interface 815 may be displayed outside the main interface 841. The texture ball interface 815 and the main interface 841 may be displayed via a same visualization device or different visualization devices of the human interface device 130. The texture ball interface 815 and the main interface 841 may be operated through a same input device or different input devices of the human interface device 130.

FIGS. 9-a is a flowchart illustrating an exemplary process of associating an image with a texture model according to some embodiments of the present application. Process 900 may be an exemplary description of a possible embodiment of 510 in FIG. 5. One or more operations of the process 900 may be performed by the devices illustrated in FIG. 2-a and/or FIG. 2-b.

In 901, an image may be displayed in a first region of the interface. The first region may be a region or an interface element for displaying an image to be processed on the user interface 700 (e.g., a region displaying an image or local image to be processed in the image section 701). The image may be a whole image to be processed (e.g., the image 730) or a local image obtained through 460 based on a global image (e.g., the image 730). The first region may be the image to be processed itself or an approximate region in which the image to be processed is displayed. The operation 901 may be performed by the interface module 360.

In 903, an interface element corresponding to a texture model may be displayed in a second region of the interface. The second region may be a region or an interface element for displaying a texture ball 750 on the user interface 700. The second region may be the texture ball itself or an approximate region in which the texture ball is displayed. The operation 903 may be performed by the interface module 360.

The operation 901 and the operation 903 may be performed in any sequence. The operation 901 and the operation 903 may also be performed simultaneously.

In 905, a directional operation in a direction from the second region to the first region may be performed between the first region and the second region. The directional operation may start from the second region (a texture ball)

or its approximate position, and end at the first region (the image to be processed) or its approximate position. The directional operation may be a single operation, an operation combination including a series of operations (for example, a combination of a voice operation, a key operation, or the like), or one or more operations included in an operation combination. In some embodiments, before or during the directional operation, operations for selecting the first region (or the image to be processed), selecting the second region (or the texture ball) and/or confirming the association therebetween may be optionally included. The operation 905 may be performed through the peripheral device 213.

The process 900 may be further graphically described by FIG. 9-*b*. As shown in FIG. 9-*b*, Image 910 may be a specific embodiment of the image 730. The image 910 may be a global image. Image 930 may be a local image of the image 910. The image 930 may represent an object (e.g., a heart). The image 930 may be obtained through image segmentation or user selection based on the image 910. Texture ball interface 920 may be a specific embodiment of the texture ball interface 760. Texture ball 925 may be a specific embodiment of the texture ball 750. Pointer 940 may be a specific embodiment of the pointer 720.

In order to associate the texture model represented by the texture ball 925 with the image 930, a directional operation in a direction from the texture ball 925 to the image 930 may be performed. Taking a dragging operation as an example, the dragging operation may be performed through an input component of the human interface device 130, such as a mouse, a touch screen, a touch pad, a joystick, a remote control, or the like. The input component may include at least one button (for the touch screen or the touch pad, or the like, the button may refer to the touch screen or the touch pad itself). The dragging operation may include at least one following operation: moving the pointer 940 onto the texture ball 925 by using the input component (for the operation performed via a touch screen, the pointer 940 may refer to a finger); pressing a button on the input component (for the touch screen or the touch pad, pressing the button may represent that the finger does not leave the touch screen or the touch pad); moving the pointer 940 from the texture ball 925 onto the image 930 by using the input component; releasing the button (for the touch screen or the touch pad, releasing the button may represent that the finger leaves the touch screen or the touch pad).

In some embodiments, in at least one operation of the dragging operation, an image 945 may be displayed on the pointer 940. The image 945 may be a corresponding visual presentation, contour, or shadow of the texture ball 925. In some embodiments, after the dragging operation is completed, the user interface 700 may further display a secondary interface 710 to inform the user to confirm the association operation of the image and texture model. In some embodiments, before starting the dragging operation, at least one operation of displaying the texture ball interface 920 may be included. In some embodiments, before starting the dragging operation, the user may need to select the image 930 through the input component. For example, the user may select the image 930 by moving the pointer 940 onto the image 930 and pressing the button one or more times.

FIGS. 9-*c* is a flow chart illustrating an exemplary process of associating an image with a texture model according to some embodiments of the present application. Process 950 may be an exemplary description of a possible embodiment of 510 in FIG. 5. Operations of the flow 950 may be performed by the devices illustrated in FIG. 2-*a* and/or FIG. 2-*b*.

In 951, an image may be displayed in a first region of the interface. The first region may be a region or an interface element for displaying an image to be processed on the user interface 700 (e.g., a region displaying an image or local image to be processed in the image section 701). The image may be a whole image to be processed (e.g., the image 730) or a local image obtained through 460 based on a global image (e.g., the image 730). The first region may be the image to be processed itself or an approximate region in which the image to be processed is displayed. 901 may be performed by the interface module 360.

In 953, an image to be processed may be selected. The selection may be performed through an operation such as clicking, hovering, dragging, box-drawing, clicking on a key of a controller, voice selection, gesture determination, focus determination, or the like. Optionally, the process of selection may further include the operation of confirming the selection. In some embodiments, optionally, selecting the image to be processed may trigger 955. The operation 953 may be performed through the peripheral device 213.

In 955, an interface element corresponding to a texture model may be displayed in a second region of the interface. The second region may be a region or an interface element for displaying a texture ball 750 on the user interface 700. The second region may be the texture ball itself or an approximate region in which the texture ball is displayed. The operation 955 may be performed by the interface module 360.

In 957, the interface element may be selected. The interface element may be a texture ball. The selection may be performed through an operation, such as clicking, hovering, dragging, box-drawing, clicking on a key of a controller, voice selection, gesture determination, focus determination, or the like. Optionally, the process of selection may further include the operation of confirming the selection. In some embodiments, the association operation may be completed through the operation of selecting the texture ball itself. The operation 953 may be performed through the peripheral device 213.

In the process 950, the sequence of operations 951 to 957 may be adjusted. For example, the operation 951 and the operation 955 may be performed first, and then the operation 953 and the operation 953 may be performed. As another example, the operation 957 may be performed first, and then the operation 953 may be performed. Selecting the image to be processed and selecting the interface element may form the basis of the association operation of the operation 510.

The process 950 may be further graphically described by FIG. 9-*d*.

In FIG. 9-*d*, image 912 is a specific embodiment of the image 730, and the image 912 may be a global image. Image 932 may be a local image of the image 912. The image 932 may represent an object (e.g., a heart). The image 932 may be obtained through image segmentation or user selection based on the image 912. Texture ball interface 922 may be a specific embodiment of the texture ball interface 760. The texture ball 926 may be a specific embodiment of the texture ball 750. The pointer 942 may be a specific embodiment of the pointer 720.

The association operation may be performed through an input component of the human interface device 130, such as a mouse, a touch screen, a touch pad, a joystick, a remote control, or the like. The input component may include at least one button (for the touch screen or the touch pad, or the like, the button represents the touch screen or the touch pad itself). The operation of associating the texture model represented by the texture ball 926 with the image 932 may include at least one operation: moving the pointer 942 onto the image 932 by using the input component; pressing a button of the input component one or more times to select the image 932; moving the pointer 942 onto the texture ball 926 by using the input component; clicking on the texture ball 926 one or more times. In some embodiments, after the association operation is completed, the user interface 700 may further display a secondary interface 710 to inform the user to confirm the operation of associating the image with the texture model. In some embodiments, between the two operations of selecting the image 932 and moving the pointer 942 onto the texture ball 926, the process of the association operation may include at least one operation of displaying the texture ball interface 922.

It should be noted that the association operation of the texture ball and the image on the interface may include various methods, and FIGS. 9-a to 9-d are only provided for illustration purposes, and not intended to limit the specific form of the association. The association operation of the texture ball and the image on the interface may also be performed in other forms, such as the voice operation. The user may complete the association operation by inputting a voice command through an intelligent voice input system, for example, "associating the No. 13 texture ball with the No. 2 image", or the like.

FIG. 10-a is a flowchart illustrating an exemplary process of associating a local image with a texture model according to some embodiments of the present application. Process 1050 may be an exemplary description of a possible embodiment of 480 in FIG. 4-b. Operations of the process 1050 may be performed by the devices illustrated in FIG. 2-a and/or FIG. 2-b.

In 1051, a first local image may be obtained. The obtaining the first local image may be performed by selecting a local image (e.g., the first local image) obtained in 460. The selection manner may be an operation, such as clicking, hovering, dragging, box-drawing, clicking on a key of a controller, voice selection, gesture determination, focus determination, or the like. Optionally, the process of selection may further include the operation of confirming the selection. The acquiring the first local image may also be performed by displaying one or more local images including the first local image obtained in 460 on the user interface 160 (e.g., the image section 701). The obtaining the first local image may be processed by performing 460 once again (for example, performing the image selecting operation or the image segmentation operation once again).

In 1053, a first texture model may be selected from one or more texture models. The one or more texture models may be displayed on the user interface 160 (e.g., the texture ball interface 760) in the form of one or more texture balls (e.g., the texture ball 750) with a one-to-one correspondence. Optionally, the category of the displayed one or more texture balls (or the texture model) may be determined based on the object category corresponding to the first local image. A texture ball corresponding to the first texture model may be selected through a manner such as clicking, hovering, dragging, box-drawing, clicking on a key of a controller, voice selection, gesture determination, focus determination, or the like. Optionally, the process may further include the operation of confirming the selection.

In 1055, the first texture model may be associated with the first local image. Detailed association approaches may be found in FIGS. 5 and 9-a to 9-d and the related descriptions.

In some embodiments, a second local image and a second texture model may be selected and associated by repeating the process 1050. The second local image may or may not include one or more pixels/voxels of the first local image. The second texture model and the first texture model may be same or different.

The process of associating a plurality of local images with a plurality of texture models may be further graphically described through FIGS. 10-b and 10-c.

FIGS. 10-b and 10-c illustrate schematic diagrams of associating at least one texture ball with a plurality of local images on an interface according to some embodiments of the present application. The association of a texture ball with a local image may be performed automatically or manually. Detailed information may be found in related descriptions of FIGS. 4-a, 4-b, 5, and 9-a to 9-d. In FIGS. 10-b and 10-c, image 1000 is a specific embodiment of the image 730, and the image 1000 may be a global image. Image 1010 and image 1020 may be local images of the image 1000. The image 1010 and the image 1020 may each represent an object. For example, the image 1010 may represent a heart, and the image 1020 may represent a liver. The image 1010 and the image 1020 may be obtained through image segmentation or user selection based on the image 1000. More detailed descriptions may be found in the related descriptions of FIGS. 4-a and 4-b. Texture ball 1030 and texture ball 1040 may each be a specific embodiment of the texture ball 750. The texture ball 1030 and the texture ball 1040 may be displayed on a same or different texture ball interfaces 760. The texture ball 1030 and the texture ball 1040 may be a same or different texture balls. FIGS. 10-b and 10-c introduce two different methods for associating the texture ball 1030 with the local image 1010 and associating the texture ball 1040 with the local image 1020.

In FIG. 10-b, each time when a local image is obtained, a texture ball may be associated with the local image. Taking the association operation between two texture balls and two local images, the following operations may be specifically included: obtaining the image 1010 based on the image 1000. Associating the texture ball 1030 with the image 1010 automatically or manually. After the completion of this operation, the image 1010 may be transformed into the image 1011, and the image 1000 may be transformed into the image 1001 accordingly. Acquiring the image 1020 based on the image 1001. Associating the texture ball 1040 with the image 1012 automatically or manually. After the completion of this operation, the image 1020 may be transformed into the image 1021, and the image 1001 may be transformed into the image 1002 accordingly.

In FIG. 10-c, after a plurality of desired local images are obtained, the operations of associating the texture balls with these local images may be performed together. Taking the association operation between two texture balls and two local images as an example, the following operations may be specifically included: acquiring the image 1010 and the image 1020 via one or more operations based on the image 1000. Associating the texture ball 1030 with the image 1010 automatically or manually. After the completion of this operation, the image 1010 may be transformed into the image 1011, and the image 1000 may be transformed into the image 1001 accordingly. Associating the texture ball 1040 with the image 10120 automatically or manually. After completion of this operation, the image 1020 may be transformed into the image 1021, and the image 1001 may be transformed into the image 10021 accordingly. In some embodiments, after the image 1010 and the 1020 is obtained, the image 1010 and the image 1020 may be selected simultaneously and both of these two images may be associated with one texture ball 1030 (or a texture ball 1040).

In the association operation illustrated in FIGS. 10-*b* and 10-*c*, the image 1010 and the image 1020 may be arbitrary images, and no sequent relation may exist between the associations of the two images. Although the operation result of associating a plurality of local images of a global image with the texture ball in FIGS. 10-*a* and 10-*b* may be the same, the application codes for associating an image with a texture ball in the image processing system 120 represented by FIGS. 10-*a* and 10-*b* may have great difference. The image processing system 120 represented by FIG. 10-*b* may use the association operation manner illustrated in FIG. 10-*a*, while the image processing system 120 represented by FIG. 10-*a* may not be able to use the association operation manner illustrated in FIG. 10-*b*. The image processing system 120 represented by FIG. 10-*b* may also use a combined manner of the operation manners illustrated in FIGS. 10-*a* and 10-*b*. For example, the user may determine when to perform the corresponding association operation at will, such as after one, a batch of, or all of the desired local images are generated.

Figure 11:
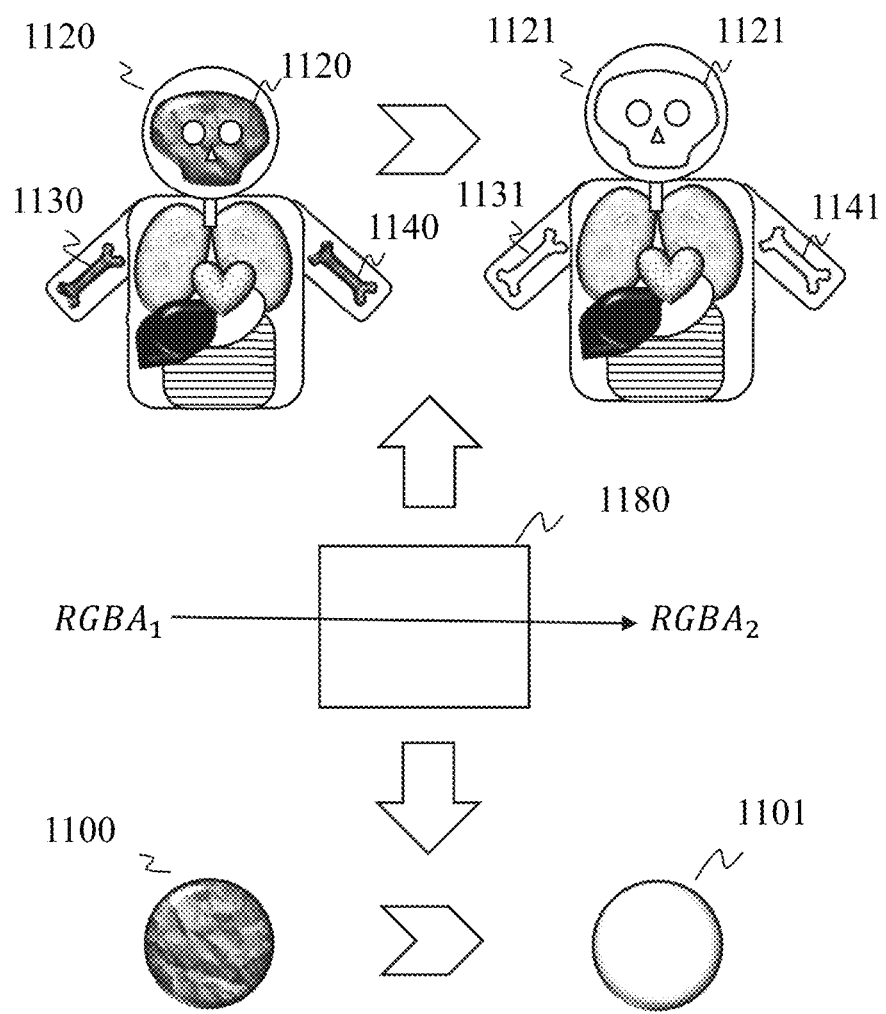
FIG. 11 illustrates a schematic diagram of the effect of editing a texture model on display effects of a texture ball and a local image associated with the texture model according to some embodiments of the present application.

FIG. 11 illustrates a schematic diagram of an effect of editing a texture model on a texture ball and a local image display effect associated with the texture model according to some embodiments of the present application. Texture ball 1100 is a specific embodiment of the texture ball 750 and represents a texture model $RGBA_1$. At least one parameter of the texture model $RGBA_1$, such as parameters relative to brightness, hue, contrast, transparency, etc., may be edited through at least one interface 1080 of the user interface 700. The interface 1180 may be a main interface or a secondary interface. After the parameter of the texture model $RGBA_1$ is edited, the texture model $RGBA_1$ may be transformed into $RGBA_2$. Accordingly, the texture ball 1100 may also be transformed into the texture ball 1101. The texture ball 1101 represents the texture model $RGBA_2$. It should be noted that the texture model $RGBA_2$ represents the texture model $RGBA_1$ with the changed parameter(s), and both of the two texture models may have a same storage location in the imaging system 100. Therefore, the recognition parameter pointing to the texture model $RGBA_1$ may point to the new texture model $RGBA_2$. The texture ball 1100 and the texture ball 1102 may be substantially the same texture ball. When the texture model $RGBA_1$ for generating the display effect has been transformed into the texture model $RGBA_2$, the display effect may be changed accordingly.

Image 1120 is a specific embodiment of the image 730. The image 1120 may include at least one local image. The at least one local image may be associated with a same texture model, or different texture models. For example, the local images 1120, 1130 and 1140 may be associated with the texture model $RGBA_1$. Therefore, before the texture model $RGBA_1$ is edited, the local images 1120, 1130 and 1140 may have the display effect as shown by the texture ball 1100. After the texture model $RGBA_1$ is transformed into the texture model $RGBA_2$, without performing any operation on the at least one local image in the image 1120, when the local images 1120, 1130 and 1140 are being displayed (for detailed operations, the related descriptions of FIG. 6 may be referenced), the obtained recognition parameter of the texture model remains to be the recognition parameter originally pointing to the texture model $RGBA_1$. As the texture model $RGBA_1$ has already been edited to be the texture model $RGBA_2$, and both of the two texture model have a same storage location in the imaging system 100, the recognition parameter may now point to the texture model $RGBA_2$ Therefore, when the local images 1120, 1130 and 1140 is displayed or outputted, the texture model $RGBA_2$ may be used to determine the output color, and they are displayed as the local images 1121, 1131 and 1141. The local images 1121, 1131 and 1141 may have the display effect illustrated by the texture ball 1101. The images 1121, 1131 and 1141 are substantially still the local images 1120, 1130 and 1140.

It is noted that, the present application is described by way of example with reference to an adjustment of color. However, it is understood that the principle of the present application may be applied to adjust other properties or parameters of an image/pixel/voxel, such as grayscale, brightness, contrast, saturation, hue, transparency, refractive index, reflectivity, shiness, ambient light, diffuse light, specular effect, or the like, or a combination thereof. A texture model or a set of texture models may be applied for generating the corresponding parameter(s) (or be referred to as output parameter(s)). The obtained output parameters may then be used to generate the output image.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "block," "module," "sub-module," "engine," "unit," "sub-unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, means, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer as a stand-alone software package, partly on the user's computer and partly on a remote computer or entirely on the remote computer or server. In the latter scenario, the remote computer may connect to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the application, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numerical parameters used in the specification and claims are approximations and the approximations may be changed depending on the desired characteristics of the individual embodiments. In some embodiments, the numerical parameters should take into account the prescribed effective digit and use a general permutation method. Although the numerical ranges and parameters used to confirm the breadth of its range in some embodiments of the present application are approximations, in certain embodiments, the setting of such values is as accurate as possible within the feasible range.

Each patent, patent application, patent application publication and other materials cited herein, such as articles, books, instructions, publications, documents, etc., are hereby incorporated by reference in their entirety. In addition to the application history documents that are inconsistent or conflicting with the contents of this application, the widest range of limited documents (currently or later attached to this application) is excluded from the application. It is to be noted that if the description, definition, and/or terminology used in the appended application of this application is inconsistent or conflicting with the contents described in this application, the description, definition and/or terminology of the present application may be used.

Finally, it is to be understood that the embodiments described in this application are merely illustrative of the principles of the embodiments of the present application. Other variations may also be within the scope of this application. Accordingly, by way of example, and not limitation, alternative configurations of embodiments of the present application may be considered consistent with the teachings of the present application. Accordingly, embodiments of the present application are not limited to the embodiments that are expressly described and described herein.

What is claimed is:

1. A system, comprising:
a data obtaining device;
a storage device;
a processor; and
instructions, being stored in the storage device, when executed by the processor, causing the system to perform operations including:
    obtaining, by the data obtaining device, an image including an object, the image including at least one pixel or voxel;
    identifying, by an identification unit in the processor, a category of the object, the category representing a tissue or an organ corresponding to the object;
    causing, via an interface, at least one interface element corresponding to at least one candidate texture model to be displayed based on the category of the object, wherein the at least one candidate texture model is selected, based on the category of the object, from a library including a plurality of candidate texture models that correspond to a plurality of candidate categories, the plurality of candidate categories including a bone, a vessel, a muscle, an interior organ, a nerve, or a combination thereof;
    receiving, via the at least one interface element, a selection of a texture model from the at least one candidate texture model;
    associating the image with the texture model;
    determining an output parameter of the at least one pixel or voxel based on the texture model associated with the image; and
    generating an output image based on the output parameter of the at least one pixel or voxel.

2. A method implemented on at least one device, each of which has at least one processor and one storage device, the method comprising:
obtaining an image including an object, the image including at least one pixel or voxel;
identifying, by an identification unit in the processor, a category of the object, the category representing a tissue or an organ corresponding to the object;
causing, via an interface, at least one interface element corresponding to at least one candidate texture model to be displayed based on the category of the object, wherein the at least one candidate texture model is selected, based on the category of the object, from a library including a plurality of candidate texture models that correspond to a plurality of candidate categories, the plurality of candidate categories including a bone, a vessel, a muscle, an interior organ, a nerve, or a combination thereof;

receiving, via the at least one interface element, a selection of a texture model from the at least one candidate texture model;

associating the image with the texture model;

determining an output parameter of the at least one pixel or voxel based on the texture model associated with the image; and generating an output image based on the output parameter of the at least one pixel or voxel.

3. The method of claim 2, the texture model including at least one color parameter, the method further comprising:
determining the output parameter of the at least one pixel or voxel of the image based on the at least one color parameter.

4. The method of claim 2, the associating the image with the texture model comprising:
displaying the image in a first region of the interface;
displaying the interface element corresponding to the texture model in a second region of the interface; and
performing a directional operation in a direction from the second region to the first region.

5. The method of claim 2, the associating the image with the texture model comprising:
displaying the image in a first region of the interface;
selecting the image;
displaying the interface element corresponding to the texture model in a second region of the interface; and
selecting the interface element.

6. The method of claim 2, further comprising:
obtaining the image based on a global image, the image being a part of the global image.

7. The method of claim 6, further comprising:
obtaining the image by performing a segmentation on the global image based on a segmentation algorithm.

8. The method of claim 2, the identifying the category of the object comprising:
identifying the category of the object based on a segmentation algorithm.

9. The method of claim 2, the category of the object including at least one of a bone, a vessel, a muscle, an interior organ, or a nerve.

10. The method of claim 2, the identifying the category of the object comprising:
matching the image with a standard image; and
identifying the category of the object based on the matching result.

11. The method of claim 6, further comprising:
obtaining a first image based on the global image;
obtaining a second image based on the global image;
selecting a first texture model from the at least one candidate texture model;
associating the first texture model with the first image;
selecting a second texture model from the at least one candidate texture model;
associating the second texture model to the second image;
determining a color of at least one pixel or voxel of the first image based on the first texture model and generating a first output image therefrom;
determining a color of at least one pixel or voxel of the second image based on the second texture model and generating a second output image therefrom;
generating a third output image based on the global image, the third output image including the first output image and the second output image.

12. The method of claim 11, wherein:
the first texture model is the same as the second texture model; and
the colors of the pixels or voxels of the first output image and the second output image change are in accordance with an editing of the first texture model or the second texture model.

13. A non-transitory computer readable medium, storing instructions, the instructions when executed by a processor, causing the processor to execute operations comprising:
obtaining an image including an object, the image including at least one pixel or voxel;
identifying, by an identification unit in the processor, a category of the object, the category representing a tissue or an organ corresponding to the object;
causing, via an interface, at least one interface element corresponding to at least one candidate texture model to be displayed based on the category of the object, wherein the at least one candidate texture model is selected, based on the category of the object, from a library including a plurality of candidate texture models that correspond to a plurality of candidate categories, the plurality of candidate categories including a bone, a vessel, a muscle, an interior organ, a nerve, or a combination thereof;
receiving, via the at least one interface element, a selection of a texture model from the at least one candidate texture model;
associating the image with the texture model;
determining an output parameter of the at least one pixel or voxel based on the texture model associated with the image; and
generating an output image based on the output parameter of the at least one pixel or voxel.

14. The system of claim 1, wherein the image is at least a part of a medical image, and the data obtaining device includes at least one of a computed tomography (CT) device or a magnetic resonance imaging (MRI) device.

15. The system of claim 1, further comprising:
a visualization device configured to display the interface, the at least one interface element presenting at least one display effect of the at least one candidate texture model respectively, wherein the output image is displayed via the interface; and
an input device, wherein the texture model is selected via the input device.

16. The system of claim 1, wherein the operations further comprise:
obtaining the image by performing a segmentation on a global image based on a segmentation algorithm.

17. The system of claim 1, wherein the identifying the category of the object comprises:
identifying the category of the object based on a segmentation algorithm.

18. The system of claim 1, wherein the identifying the category of the object comprises:
matching the image with a standard image; and
identifying the category of the object based on the matching result.

19. The system of claim 1, the category of the object including at least one of a bone, a vessel, a muscle, an interior organ, or a nerve.

\* \* \* \* \*